United States Patent [19]

Djordjevich et al.

[11] Patent Number: 4,562,843

[45] Date of Patent: * Jan. 7, 1986

[54] SYSTEM FOR DETERMINING CHARACTERISTICS OF BLOOD FLOW

[76] Inventors: Ljubomir Djordjevich, 4170 Marine Dr., Chicago, Ill. 60613; Max S. Sadove, 1021 Lathrop Ave., River Forest, Ill. 60305

[*] Notice: The portion of the term of this patent subsequent to Mar. 20, 2001 has been disclaimed.

[21] Appl. No.: 280,321

[22] Filed: Jul. 6, 1981

Related U.S. Application Data

[63] Continuation-in-part of Ser. No. 191,387, Sep. 29, 1980, Pat. No. 4,437,469.

[51] Int. Cl.$^4$ .................................................. A61B 5/02
[52] U.S. Cl. .................................. 128/672; 128/677; 128/693; 128/713; 128/734
[58] Field of Search .................. 128/713, 670–675, 128/734, 693, 713, 677

[56] References Cited

U.S. PATENT DOCUMENTS 3,920,004 11/1975 Nakayama ............... 128/691 X
3,996,925 12/1976 Djordjevich .................. 128/693
4,203,451 5/1980 Panico .................. 128/672

OTHER PUBLICATIONS

Berne, R. M. et al., "Cardiovascular Physiology", C. V. Mosby Co., St. Louis, 1972, pp. 96–97.

Primary Examiner—Kyle L. Howell
Assistant Examiner—Francis J. Jaworski
Attorney, Agent, or Firm—Fitch, Even, Tabin & Flannery

[57] ABSTRACT

Method and apparatus are disclosed for determination and display of hemodynamic characteristic values of a patient in a variety of statistical forms and in relative or absolute terms, the measurement determination being made by non-invasive impedance plethysmography under control of a central processor. A characteristic value representative of variation of blood vessel cross-sectional area is measured across a patient's body section, blood pressure is measured in the body in simultaneity with the characteristic value, and signals representative of the characteristic value and blood pressure are then processed to obtain the hemodynamic characteristic values.

80 Claims, 29 Drawing Figures

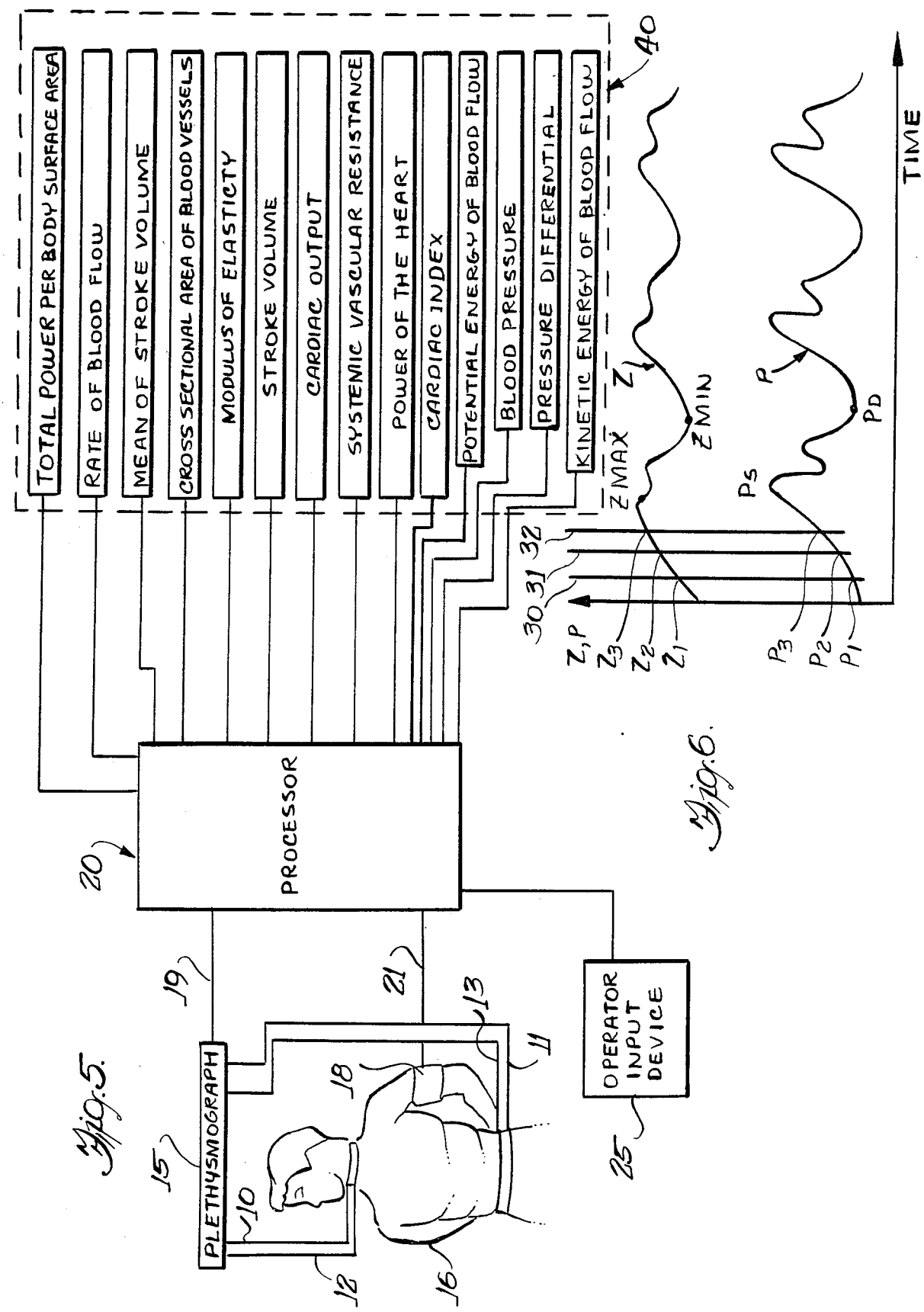

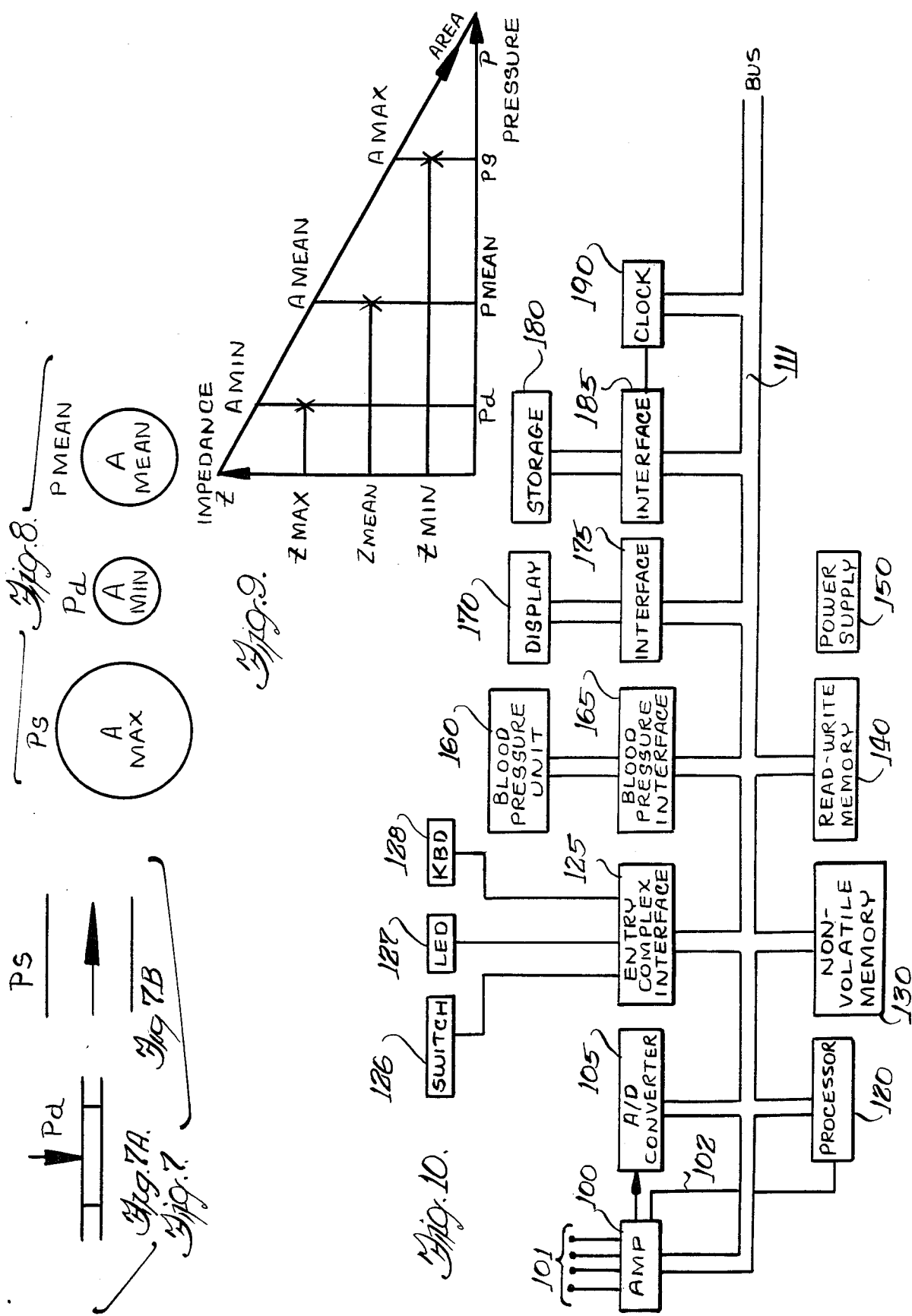

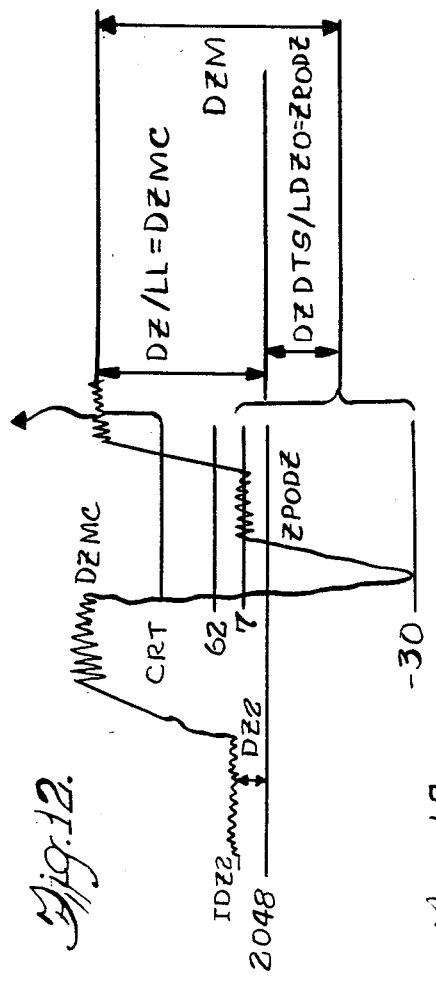
Fig. 12.
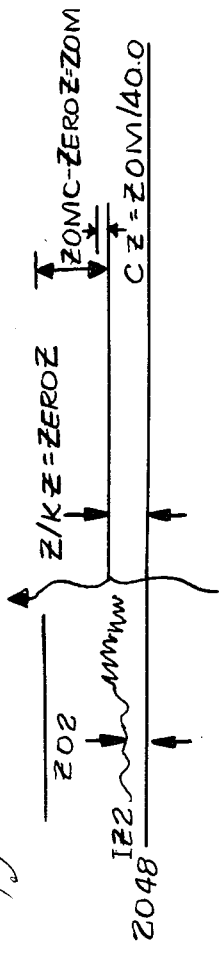
Fig. 14.
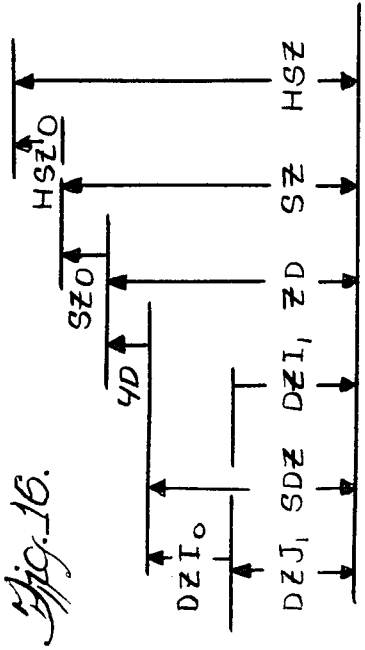
Fig. 16.
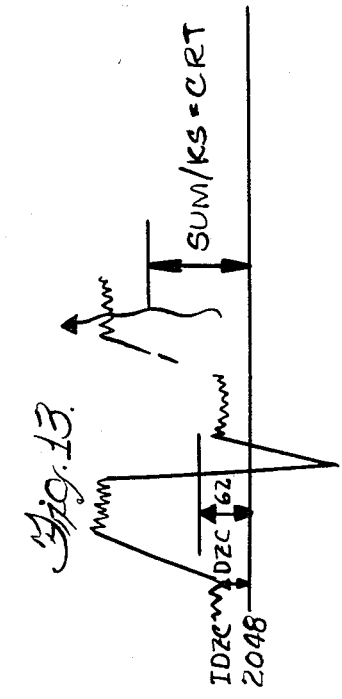
Fig. 13.
Fig. 11.
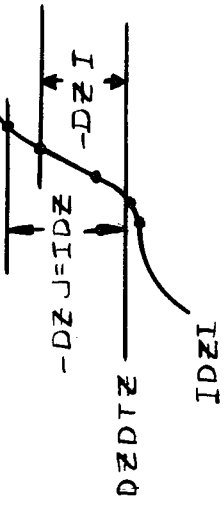
Fig. 15.

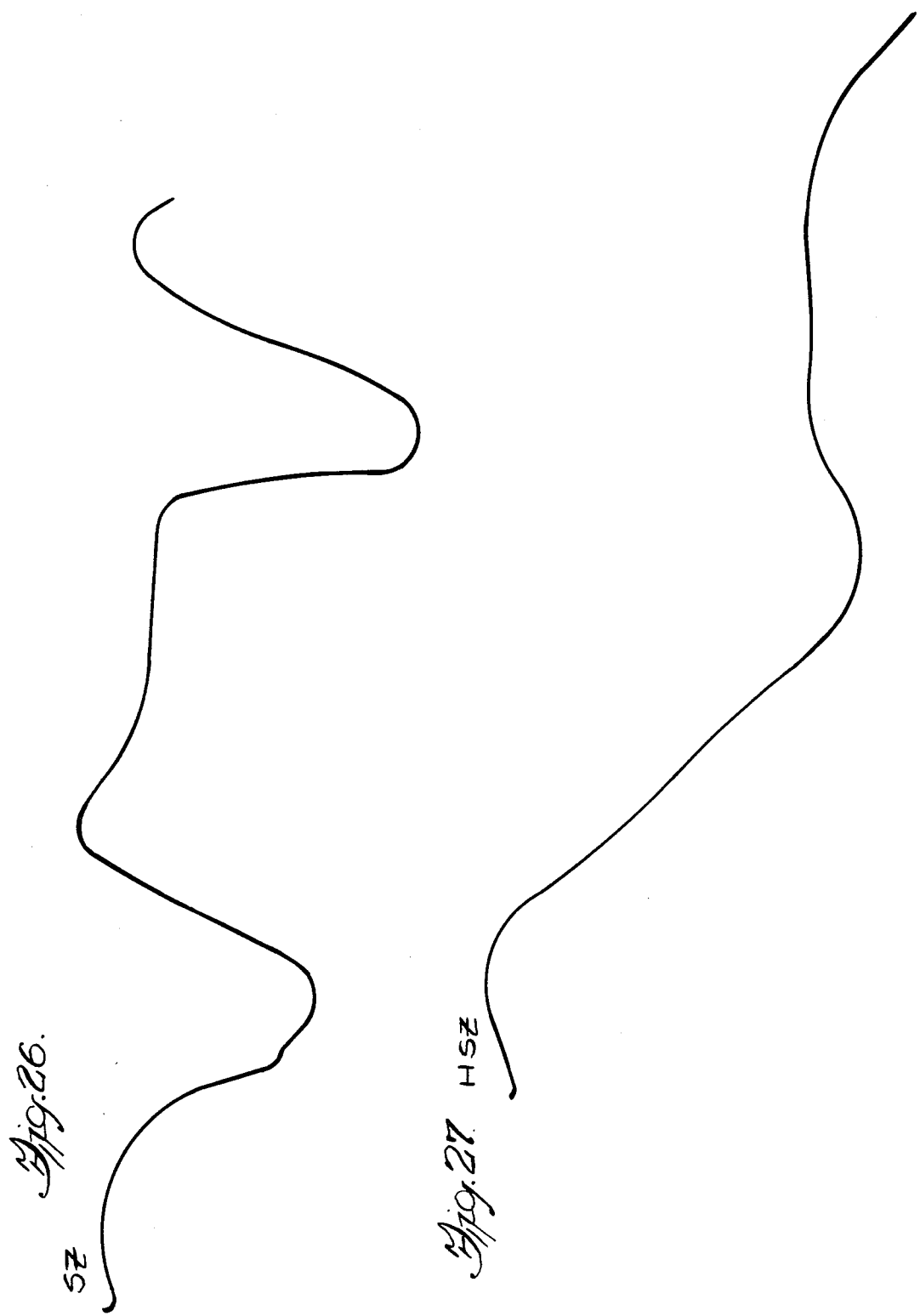

SYSTOLIC PRESSURE ENTRY IS 120
DIASTOLIC PRESSURE ENTRY IS 80
MEAN ARTERIAL PRESSURE ENTRY IS 45
PULSE RATE ENTRY IS 60
H PARAMETER ENTRY IS 150
CYCLE TIME ENTRY (IN MINUTES) IS 3
STUDY CODE ENTRY IS D

Fig. 28.

| 3-23-80 | | 11:00 A.M. | |
|---|---|---|---|
| STUDY CODE | O | PATIENT ID | 123456 |
| CARDIAC OUTPUT (L/MIN) | 7.78 | SEX | MALE |
| STROKE VOLUME (CC) | 129.6 | AGE | 28 |
| USEFUL POWER LEFT HEART (WATTS) | 1.88 | HEIGHT (CM) | 183 |
| PULSE RATE (BEATS/MIN) | 60 | WEIGHT (KG) | 75.8 |
| SYSTOLIC PRESSURE (MMHG) | 120 | ELECTRODE SEP (CM) | 27.9 |
| DIASTOLIC PRESSURE (MMHG) | 80 | BODY SURFACE AREA (M·M) | 1.97 |
| ZO (OHMS) | 22.2 | | |

| PARAMETER | VALUE | % DEVIATION FROM NORMAL | % RANGE OF NORMAL | REFERENCE PARAMETER |
|---|---|---|---|---|
| CARDIAC INDEX | 3.94 | 11 | 14/-12 | AGE |
| SYSTEMIC VASCULAR RESISTANCE | 8.76E+02 | -12<br>-13 | 17/-18<br>15/-12 | AGE<br>PRESSURE |
| CARDIAC POWER INDEX | 0.95 | 6<br>10 | 23/-18<br>19/-14 | AGE<br>PRESSURE |
| DZ/DT | 1.93 | 1 | 30/-33 | ZO |
| ELASTIC INDEX | 25-02 | -17<br>-17 | 15/-14<br>18/-14 | AGE<br>PRESSURE |
| ELASTIC MODULUS | .78E+06 | -28<br>-30 | 34/-29<br>33/-29 | AGE<br>PRESSURE |
| RATE OF ENERGY OUTPUT | 87E+04 | 39<br>14 | 19/-17<br>19/-17 | AGE<br>PRESSURE |
| RATE OF IMPEDANCE CHANGE | 1.36E+00 | 25<br>29 | 33/-27<br>30/-27 | AGE<br>PRESSURE |
| RATE OF PRESSURE CHANGE | 4.43E+06 | -6<br>-7 | 30/-28<br>32/-28 | AGE<br>PRESSURE |

SYSTEM FOR DETERMINING CHARACTERISTICS OF BLOOD FLOW

CROSS REFERENCE TO RELATED APPLICATIONS

The present application is a continuation in part of preceeding application Ser. No. 191,387 filed on Sept. 29, 1980 now U.S. Pat. No. 4,437,469.

This invention relates to a process and apparatus for determining hemodynamic characteristics from the monitoring of the flow of blood in a section of the living body. More particularly, this invention relates to a process and apparatus in which an electrical characteristic value representative of at least the variance in cross sectional area of a blood vessel is measured across the section of living body, simultaneously with the measurement of blood pressure, wherein the measured values are utilized in combination with a set of hemodynamic equations to produce an output representation of the hemodynamic characteristics of the living body.

Heretofore, a number of methods and means have been devised and utilized for determining blood flow characteristics. These include indicator dilution methods, magnetic flow meters, ultrasonic blood flow meters, impedance cardiography, blood flow determination by radiographic methods, blood flow determination by catherization known as the Swan Ganz method, and blood flow determination by simultaneous blood sampling from a vein and an artery coincident with measurement of oxygen consumption known as the Fick method. The two most widely used methods are the Swan Ganz and Fick methods. These methods are supported by long-established empirical data, and are held in high esteem, being more reliable and repeatable than the other mentioned methods and means are.

The above methods and means all have problems and inadequacies in meeting the needs of surgeons, patients, and others in medical practice. A major objection to most of the existing methods is the lack of accuracy, repeatability, and supporting empirical data. Swan Ganz and Fick methods are the most widely accepted and used, but are invasive techniques requiring insertion of foreign objects into the body and blood stream. While these methods give an approximate repeatability variation of plus and minus 6%, better than other preexisting methods, these methods are relatively dangerous to the patient. With both the Swan Ganz and Fick invasive methods, there is potential for infection and local tissue damage as a result of the measurement process. Because of this, patient acceptance of these methods is limited, and the use of these methods is restricted to very serious cases. Additionally, the Swan Ganz method can result in potential cardiac irregularities, and pulmonary injuries, as well as potential damage to the lungs and veins (puncture). Since the Fick and Swan Ganz methods are dangerous to the patient's well being, the amount of time the invasive means may be utilized is limited. Continuous measurements and sequential measurements are not practicably possible, as prolonged or repeated insertion of the invasive means into the patient's body and blood stream is potentially harmful, traumatic, discomforting and relatively dangerous to the patient. Thus, a small number of discrete samples are taken, which can be quite unsuitable in unstable patients, as this can lead to large errors.

Special skills are required for utilizing invasive blood flow measurement, such as the Swan Ganz or Fick methods, and therefore utilization of these methods is generally restricted to the catherization lab, operating room, and to a limited extent to the cardiac critical unit. These techniques are not utilized, as a rule, in the patient's room, on out-patients, or in a doctor's office, due to the hazardous and traumatic nature of these techniques of measurement. Additionally, these methods create discomfort and pain in the patient being tested. Thus, these methods are typically restricted to patients who are in acute state, and are not generally utilized for patients undergoing preventive check-up, rehabilitation, or in a chronic disease states.

In U.S. Pat. No. 3,996,925, by one of the present inventors, a system is disclosed for determining blood flow as a function of the electrical impedance measured across a section of the living blood in accordance with an analogue electronic processor. This system provided for the determination of stroke volume and cardiac output, utilizing the measured impedance value over a given time and utilizing a number of constant values (not measured) representing physiological and personal characteristics of the patient. However, there is a long standing need for a system which is more accurate, and which is effective for determining other hemodynamic characteristics and which is responsive to actual personal characteristics of the patient and the section of the body across which measurements are made. For example, it would be desirable to determine a value individually for each patient based on measured values, instead of assuming a constant value for all patients.

The mathematical analysis of circulation is formulated in hemodynamics. It is a combination of fluid mechanics and the theory of elasticity applied to the pulsating flow of blood through blood vessels and the corresponding periodic displacements of vascular walls. The main problem in the application of hemodynamics to clinical measurements is how to obtain reliable values of important hemodynamic parameters, such as diameters of arteries, modulus of elasticity of arterial walls, length of blood vessels, etc.

Electrical impedance plethysmography can be combined with hemodynamics. Electrical impedance plethysmography is based on the measurement of transthoracic impedance Z and its first time derivative DZ/DT, which in accordance with hemodynamic theory provide valuable information about intravascular and extravascular fluid volume, heart function, and vascular response to the heart function.

Variation of electrical impedance of a section of the human body as a function of time is the basis of impedance plethysmography. The resultant form of the impedance signal is related to a timing parameter and events in the cardiac cycle to deduce stroke volume by applying a single semi-empirical formula such as that derived by Kubicek, as set forth in the annals of N.Y. Academy of Science, 1970, page 729, to the geometrical parameters of the wave-form. One problem with this technique is that very limited cardiovascular data is obtainable. Another, more serious, limitation and problem with this method is that of accuracy.

Utilization of hemodynamics for modeling requires specific numerical values of various coefficients which are a part of the model, but which depend on individual characteristics of the patient and of the selected part of the body, such as diameters and lengths of arteries, elastic moduli of their walls, thickness of the walls, etc.

All these characteristics vary from the patient and from one location in the body to another.

The elastic properties of the vascular system are represented by the modulus of elasticity, which is defined as the ratio of stress and strain. The elastic properties of arteries depend on several factors such as the degree of arteriosclerosis, blood pressure, and vasoconstriction and vasodilation. Sclerotic changes of arterial walls cause intrinsic changes of mechanical properties and relative thickness of the walls. They increase the modulus of elasticity. Modulus of elasticity is a nonlinear monotonically increasing function of blood pressure in the physiological range. Any agent (neurogenic, hormonal, drug) which causes vasoconstriction will effectively increase the apparent modulus of elasticity. A vasodilator will cause an effective decrease of the modulus. Thus, the measured apparent modulus depends on the vascular tone of the patient under test. These factors, and others, are the main reasons why a fixed value cannot be assumed for all patients for modulus of elasticity. Rather, the modulus of elasticity should be calculated individually for each patient based upon measured values. Only in this way can the mathematical model be properly utilized in computing hemodynamic characteristics from measured values.

Accordingly, it is an object of the present invention to provide methods and means for determining and displaying hemodynamic characteristics of a patient based on measured values from the body of the patient under test.

It is a further object to provide and display hemodynamic characteristic values, alternatively or simultaneously as absolute values, a range of values, percent deviation of values, and/or other statistical forms.

It is a further object to provide a means and method for continuous and/or sequential measurement of data to provide for the determination and display of hemodynamic characteristics related to continuous or sequential measurement.

It is still a further object to provide for the determination and display of multiple hemodynamic characteristic values utilizing noninvasive measurements.

It is a further object to utilize time correlated measured indications obtained from the body under test, and empirically established models, and a computer, to eliminate the use of most general physical constants, replacing the general physical constants with a value determined from measured values, in the method and means for determining and displaying selective hemodynamic characteristics.

It is yet another object to provide a means and method of measuring data and determining hemodynamic characteristics which has high repeatability, (exhibiting a small variation in the repeatability of results).

It is still a further object to provide a hemodynamic measurement system which achieves high patient acceptance level, which has virtually no potential for infection, local tissue damage, cardica irregularities, pulmonary injury, or lung injury, and which permits preventive medical therapy as a result of utilization of cardiovascular function data.

In accordance with the illustrated embodiments of the present invention, a method and a means for implementing the method are disclosed for measuring and displaying hemodynamic characteristics. A characteristic value representative of at least the variation in cross sectional area of a blood vessel is measured across a section of a living body, blood pressure is measured in the body simultaneously with the measurement of the characteristic value, and signals representative of the characteristic value and the blood pressure measurements are utilized (processed) to obtain an electrical signal representing the hemodynamic characteristic. In a preferred embodiment, any or all of selected hemodynamic characteristics are displayed.

Preferably the measurement of the characteristic value is done noninvasively. Alternatively, both the blood pressure and characteristic value are measured noninvasively. In the illustrated embodiment, the characteristic value measured is the electrical impedance across a section of the body. The hemodynamic characteristic is determined from measurements of the electrical characteristic and the pressure measurements in accordance with selected hemodynamic formulae. Various formulae are utilized, enabling the determination of numerous important hemodynamic characteristics such as cardiac output, cardiac index, stroke volume, cardiac power index, work of heart, elasticity, contractility, base impedance, and so forth. Furthermore, the hemodynamic characteristics may be determined as absolute values, a range of values, in terms of percent deviation from mean value, as a value over a single cycle or averages (and other statistical functions) of multiple cycles or cardiac system measurement.

In the illustrated embodiment, personal characteristics of the patient being measured are input for use by the processor in determining hemodynamic characteristics. The personal information can include age, weight, height, sex, race, the spacing distance of the plethysmograph electrodes, and/or the viscosity and resistivity of the blood of the patient under test. The viscosity and resistivity of the blood as determined by appropriate means is coupled to the means for processing (computer or logic circuitry) for use in determining and displaying hemodynamic characteristics.

Other objects and advantages of the present invention will become apparent upon reading the following detailed description, while referring to the attached drawing, in which:

BRIEF DESCRIPTION OF THE DRAWINGS

FIG. 5 is a block diagram of a system for determining hemodynamic characteristics in accordance with the present invention;

FIG. 6 is a graphical illustration of simultaneously measured values of impedance Z and measured values of pressure P against time;

FIG. 7 is a side view of a blood vessel illustrating vessel deformation (expansion and contraction) caused by blood flow;

FIG. 8 is a pictorial representation of the cross-section of the blood vessel illustrated in FIGS. 7A-B, showing the deformation of the blood vessel for different times (and pressures) during a cardiac cycle;

FIG. 9 is a sectional view illustrating the variation in the cross-sectional area of the blood vessel corresponding to the vessel deformation of FIG. 4;

FIG. 10 is a system block diagram of an embodiment of an electrohemodynamic system in accordance with the present invention;

FIGS. 11,23,24A,24B, and 25-27 are graphs illustrating the relationship between the measured electrical system parameters and the corresponding mnemonics representative of the electrical signal values as derived from the measured values and utilized in the selected formula to determine the hemodynamic characteristics; and FIG. 28 is a pictorial representation of a report printout illustrating one form which the display can take.

Figure 1:
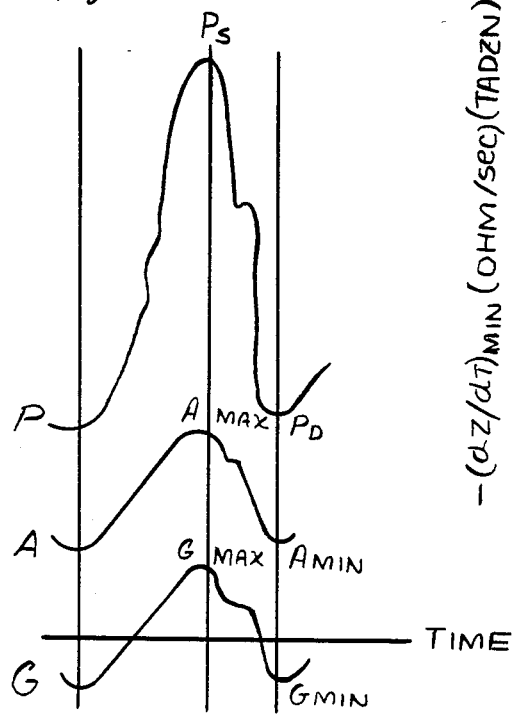
FIG. 1 is a graph plotting blood pressure, cross-sectional area of arterial lumen, and electrical conductance against a common time axis.

A Fortran listing at pages 63a et seq. provided as an illustrative embodiment of the reduction to computer program form of the techniques and teachings of the present invention.

In accordance with the present invention, a method and means is provided for measuring a hemodynamic characteristic comprising the measurement of a characteristic value across a section of a living body (such as non-invasive measurement of electrical impedance or conductance), the measurement of blood pressure in the body simultaneously with the measurement of the characteristic value, and the processing of signals representative of the characteristic value and the blood pressure measurements through an electronic device to obtain an electrical signal representing the hemodynamic charactersitic. Further, in the illustrated embodiment, the electrical signal representing the hemodynamic characteristic is utilized to display the hemodynamic characteristic. In the illustrated embodiment, the simultaneous measurements are repeated a plurality of times, and the hemodynamic characteristics are determined responsive to the plurality of simultaneous measurements. The display can be a printout, video monitor, etc., and may be alphanumeric or graphic or a combination of both. Additionally, the determined hemodynamic characteristics can trigger an alarm or activate a servo motor.

In accordance with the teachings of the present invention, a new technique (electrohemodynamics [EHD]) is disclosed herein whereby mathematical modeling of circulation is combined with the simultaneous measurements of blood pressure and a characteristic value (such as electrical conductance) of a selected part of the body. There is no need to provide a separate timing parameter as with Kubicheck. In accordance with the present invention, the characteristic value signal (such as the electrical impedance signal) is correlated to the variation of arterial blood pressure, and the equations of hemodynamics are applied, which in conjunction with the measured values determine the hemodynamic characteristics. Thus, EHD is capable of providing all of the necessary hemodynamic parameters, such as diameters of arteries, cross-sectional area cross the measured blood vessel section, modulus of elasticity of arterial walls, etc., and as a result, can be used for measuring and determining cardiac output, cardiac index, stroke volume, systemic vascular resistance, useful power or work of the heart, elastic properties of blood vessels, contractile properties of the left heart muscle, etc. The illustrated embodiment of the present invention is non-invasive and totally harmless to the patient under test, and measurements can be done continuously for an indefinite period of time, as short as for one heart beat, or as long as days at a time. These features of the present invention solve many of the problems and shortcomings of other existing methods of measuring cardiovascular functions. A key problem in the utilization of the mathematical model of hemodynamics is that the model cannot be used for precise calculation of blood flow or other hemodynamic quantities for a specific individual patient without provision being made for specific numerical values of various coefficients which are a part of the model but which depend on the individual chracteristics of the patient and selected part of the body being tested. These coefficients include diameters, lengths, and areas of the arteries, elastic moduli of their walls, thickness of the walls, etc. These characteristics vary from patient and from one location in the body to another.

The time variation of the cross sectional area of blood vessels in a body section can be reflected as a function of the corresponding time variation of blood pressure and the measurement of the electrical conductance (or other characteristic value) of a selected section of the body of a patient. Alternatively, any method or means of determining the cross-sectional area of vessels can be used. Thus, the variation in electrical conductance in conjunction with the time variation of blood pressure provides means for determining specific numerical values of missing coefficients in the mathematical models of hemodynamics which are individually characteristic for a given patient and for the specific location across which the characteristic value is measured. Thus, in accordance with the present invention, the real time simultaneous measurements of electrical impedance (conductance) and pressure variation are preferably used to calculate the hemodynamic quantities of interest, including flow of blood, vascular resistance, elastic properties of arterial walls, and energy of circulation in the section of the body where the measurements are done.

A mathematical model for EHD is derived from the mathematical description of a pulsatile flow of blood in arteries. For example, Middleman, in *Transport Phenomena in the Cardiovascular System*, New York, Weily-Interscience, 1972, page 35 et seq., provides a detailed description and derivation of equations of his theory of the pulsatile flow of blood in arteries. In the illustrated embodiment, Middleman's model is utilized as a starting point of the hemodynamic mathematical model. Mathematical analysis of the flow of blood combines the dynamics of incompressible, pulsating, viscous fluid with the theory of elasticity. The basis is that the flow of blood is through elastic ducts, and the pressure inside the ducts is variable with time. The fundamental equations of fluid dynamics which govern this kind of flow are the Navier-Stokes equations and the continuity equation. The Navier-Stokes equations represent the balance of all the forces acting on a fluid particle, such as inertial, shear (friction due to viscosity) and pressure forces. The continuity equation is the expression of conservation of mass, taking into account, the presence or absence of sources or sinks in the circulatory system. The derivation of both equations can be found in many standard textbooks on advanced fluid mechanics.

The necessary mathematical relations for a rigorous and consistent theory of hemodynamics is set forth in an article by the present inventors in the Journal of Biomedical Engineering, 1981, Vol. 3, January, pages 25-33. For greater detail references are cited therein. Three simultaneous differential equations are derived, one representing the balance of forces on a blood vessel, one representing the equation of continuity for an incompressible fluid, and one representing the equation of incompressibility for the arterial walls. Boundary conditions are analyzed at the outer wall of the blood vessel, with radius r=Ro, at the inner wall of the blood vessel, with radius r=Ri, and at the axis of flow r=O. Six boundary condition equations follow. Combining the simultaneous differential equations and boundary conditions yields a consistent and completely defined boundary value problem which has a solution in terms of Bessel functions. There are six integration constants of the solutions which form a system of linear homogeneous equations and can be solved in terms of only one unknown constant by setting the determinant of the system equal to zero, according to the theory of linear equations. This combination of simultaneous independent measurements of P and $R_i$ with the solutions of equations of hemodynamics is the essence of electrohemodynamics. It is desirable for accuracy to measure variations of $R_i$ with great precision. A suitable technique is the measurement of the variation of electrical conductance of the part of the body where the blood flow is to be measured. The reasons are:

(1) The measurements of electrical conductance can be extremely accurate;

(2) There is a perfect theoretical relationship between conductance and the corresponding conductive areas (Ohm's Law);

(3) There is corroborated and published experimental correlation between the conductance variation and the corresponding variation of the cross-sectional areas of the lumens of participating blood vessels; and (4) Measurements are totally harmless. In addition, the measurements are done in a continuous manner, and they can be applied to any single heart beat as well as to any length of time. They can be monitored on a screen or recorded on a chart or magnetic tape recorder or fed directly into a computer or microprocessor for virtually instantaneous mathematical processing. The latter is what is done in EHD.

It should be pointed out, however, that any other technique which measures variation in arterial volumes such as, for example, various types of plethysmographs, or ultrasonic devices, may be used instead of and/or in concept with measuring electrical conductance. The basic principle of combining measured signals with the equations of hemodynamics remains the same. The axial velocity of blood $v_z$, radial velocity $v_r$, and blood pressure P, are expressed as functions or independent variables t(time), z(impedance), r(radius of vessel), and a number of parameters which depend on the characteristics of blood vessels:

$$v_z = v_z(t,z,r,\nu,R_i,K,\rho,\rho_w,E,\omega, a) \quad (1)$$

$$v_r = v_r(t,z,r,\nu,R_i,K,\rho,\rho_w,E,\omega,a) \quad (2)$$

$$P = P(t,z,r,\nu,R_i,K,\rho,\rho_w,E,\omega,a) \quad (3)$$

where, in addition to the previously defined parameters, $K = R_o/R_i$ is the ratio of outer to inner diameter of the blood vessel, $\rho$ is density of blood, $\rho_w$ is density of arterial wall, $\nu$ is kinematic viscosity of blood, E is the modulus of elasticity, $\omega$ is the frequency of the pressure variation, and a is an undetermined integration constant.

The instantaneous values of the average velocity of blood $v_z(t)$, average blood pressure P(t) and the flow q(t) are obtained by integration of $v_z$ from equation (1) and p from equation (2) over the cross-sectional area of the blood vessel, taking into account the time variation of the inner diameter $R_i(t)$ of the blood vessel. However, in order to perform the integration of equations (1) and (3) it is necessary to know the values of all parameters in the equation and the time variation of $R_i(t)$. The parameters which are not known beforehand are: modulus of elasticity E, the ratio of outer to inner diameter of blood vessel K and the integration constant a. All other parameters are measurable or known beforehand: viscosity $\nu$ and density $\rho$ of blood can be calculated with sufficient accuracy from known hematocrit and temperature (as determined from a blood sample or estimated base on "norm" data). Average density of arterial walls $\rho_w$ is also known. Frequency of the pressure variation, $\omega$, is obtained from monitoring the blood pressure by independent means.

Hence, the truly unknown parameters are only K, $R_i$, E and a. They are determined by simultaneous but independent measurements of the time variation of the average blood pressure P (t), and $R_i$ (t). The time variation of $R_i$ in the illustrated embodiment can be measured by means of impedance plethysmography, as described hereafter. All unknown parameters are calculated by substituting the known, measured numerical values of simultaneous pairs of P (t) and $R_i$(t) into equation (3).

The basic law for measuring electrical conductance is Ohm's law:

$$V = I/G_e \quad (4)$$

(V is voltage in volts, I is current in amperes and $G_e$ is conductance in ohm$^{-1}$).

In the case of alternating current, conductance is a frequency dependent parameter. Conductance is a reciprocal of electrical impedance:

$$G_e = 1/Z \quad (5)$$

where Z is electrical impedance. Conductance is the physical property of material, dependent on its size and shape. For a cylindrical body of length L (cm) and cross-sectional area A (cm$^2$):

$$G_e = A/\rho_e L (\text{ohm}^{-1}) \quad (6)$$

where L is the fixed distance between the measuring electrodes and $\rho_e$ is the resistivity of the material in ohm-cm. For normal blood, measured at a frequency of 100 kHz, $\rho_e = 150$ ohm-cm.

Equation (6) shows the basic relationship between conductance and cross-sectional area A of the arterial lumen. When blood pressure rises and approaches systolic, arteries (being elastic) expand, and A increases. When blood pressure decreases and approaches diastolic, A decreases. Change of conductance is proportional to the change of A according to equation 6. When L and $\rho_e$ are known and fixed, variation of conductance $G_e$ is a direct measure of the variation of cross-sectional area of the blood vessels A.

For accuracy sake, what is measured should be only a variation of conductance due to the relative change of the cross-section of arterial lumens. The measured conductance of any portion of the body is the total conductance, composed of the conductance of blood in parallel with the conductances of all other anatomical elements in the measured section of the body. Blood, being an electrolyte, is more conductive than bone, muscle, or viscera. The expansion of blood vessels thus causes an increase in conductance. The time variation of conductance follows the variation of arterial blood pressure with high fidelity, as illustrated in FIG. 1. The similarity of the patterns in which conductance and blood pressure simultaneously vary with time, is used to separate the conductance due to the blood from the conductance of the rest of the tissues which may safely be assumed constant during the cardiac cycle. The use of a computer as in the illustrated embodiment, makes the pattern recognition and the analysis of the conductance signal simple and accurate.

Referring to FIG. 1 the relationship between blood pressure, cross-sectional area of arterial lumen and conductance is shown. Any precise technique of measuring electrical conductance or impedance may be used. An impedance cardiograph with continuous output, for example, is well suited for this purpose. For example, the transthoracic electrical impedance Z and its first derivative dZ/dt can be measured with the IFM-/Impedance Cardiograph, Model 200, and/or similar instruments.

Conductance (G) is the inverse of impedance (Z) ($G = 1/Z$). Transthoracic electrical impedance plethysmography measures transthoracic impedance Z and its first time derivative dZ/dt. Impedance Z is a time variable quantity which can be decomposed into a time average baseline component $Z_O$ which is constant, and a time variable component $\Delta Z$ which varies in synchrony with the cardiac cycle, and which is superimposed on $Z_o$ such that $$Z = Z_O + \Delta Z \, (\Omega). \tag{7A}$$

The first time derivative of Z is $$dZ/dt = d(\Delta Z)/dt (\Omega/S). \tag{7B}$$

In this equation $dZ/dt$ does not depend explicitly on $Z_O$, because $Z_O$ is constant. This simplicity is deceptive, however.

Figure 2:
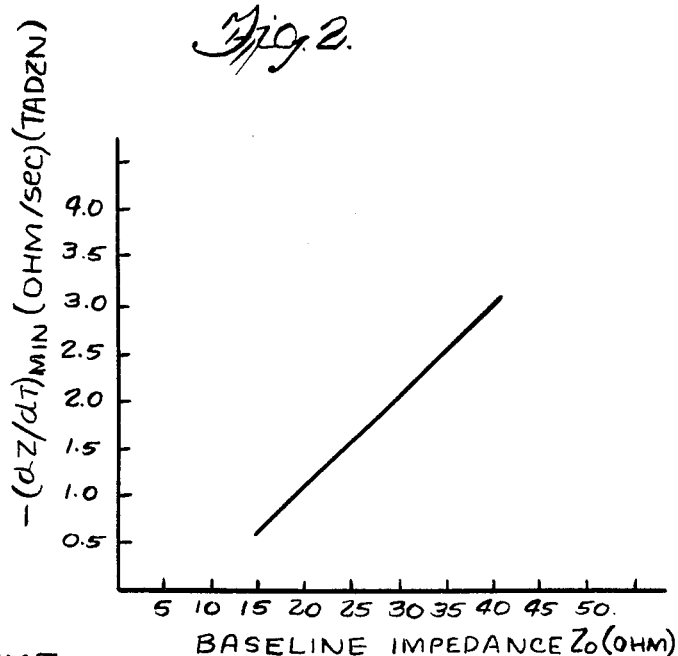
FIG. 2 is a graph showing the relationship of (dz/dt)min to Zo.

Experimental study, as set forth by the present inventors in an article in Medical Physics, Vol. 8, No. 1, Jan. Feb. 1981, pages 76 et seq., hereby incorporated by reference, herein, empirically proves that the maximum negative amplitude of the first derivative, (dZ/dt) min. is a function of $Z_O$, which implies that $\Delta Z$ is also a function of $Z_O$. The relationship of (dZ/dt)min. to ZO is shown in FIG. 2.

The numerical value of (dZ/dt)min. is of crucial importance in impedance cardiography and quantification of myocardial contractility. The functional relationship between $Z_O$ and (dZ/dt)min. if not taken into account, may lead to erroneous applications and inaccurate calculations of stroke volume, cardiac output, systemic vascular resistance, the Heather index, cardiac contractility, or any other hemodynamic parameter calculated on the basis of (dZ/dt)min.

The analytical form of the correlation of (dZ/dt)min. to $Z_O$ based on experimentally obtained date is $$(dZ/dt)\text{min.} = 0.9038 - 0.0993 Z_O. \tag{7C}$$

This equation is valid for the range of ZO greater than 19 and less than 40 ohms, which is the range of measured data. The standard deviation, the correlation coefficient between (dZ/dt)min. and $Z_O$, and the significance of the correlation are described in the Medical Physics article.

The high degree of correlation and the significance of the statistics indicate that there exists the monotonic relationship between (dZ/dt)min. and $Z_O$. This means that, statistically, the absolute value of the negative dZ/dt peak tends to increase as $Z_O$ increases. Standard deviation reflects the variability of individual peaks caused by factors other than $Z_O$. The relationship of dZ/dt to $Z_O$ is important as indicative of recovery rate.

The time of variation of Z is caused primarily by the periodic changes of blood volume inside blood vessels, which is in turn caused by the variation of blood pressure during the cardiac cycle. Hence, the amplitude and the shape of the dZ/dt signal depend primarily on the functioning of the heart. If, for example, the rate of ejection of blood from the ventricle is increased, the amplitude of the (dZ/dt)min peak is also expected to increase. However, the shape and the amplitude of the dZ/dt signal are strongly modified by the dynamic response of the vascular system to the ejection. The response depends essentially on the rate of ejection, the elastic properties of the arterial walls, the mean arterial blood pressure, the systemic vascular resistance, and the volume of blood. These factors are the consequence of the viscoelastic nature of arterial walls. The variability of these factors for different subjects accounts for the variance of the experimental data around the linear regression line as reflected in [Eq. 7C]. There are other factors, not hemodynamic in nature, which also intervene to produce Eq. (7C). Experimental data yield the statistical fact that (dZ/dt)min. tends to be larger when $Z_O$ is larger, without any apparent relationship to the ejection of blood from the ventricle. It is necessary to bear this in mind in the application of the (dZ/dt)min. measurements in the transthoracic electrical impedance plethysmography. For example, a larger (dZ/dt)min. is interpreted as a larger rate of ejection of blood from a ventricle, from which it may be deducted that cardiac contractility is larger, or that stroke volume is also larger. These conclusions may be erroneous since (dZ/dt)min. may be larger simply because $Z_O$ is larger, not the rate of ejection. A better indicator of rate of ejection and other parameters deduced from it, would be the deviation of an individual (dZ/dt)min. measurements from the value predicted by Eq. (7C) for the corresponding measured value of $Z_O$.

Figure 3:
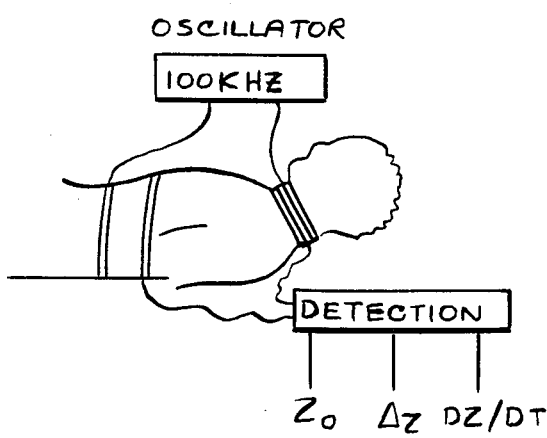
FIG. 3 is a partial block diagram illustrating one embodiment of an electrode configuration for use with the present invention.

Referring to FIG. 3, the connection and configuration of a plethysmograph hookup to a patient's body is illustrated. The measurement of the conductance is done on the part of the body where the hemodynamic parameters are to be determined. If cardiac output is desired, the measurement is done on the chest.

In the illustrated embodiment, the plethysmograph is connected to four disposable aluminized mylar strip electrodes (tetrapolar arrangement) with an adhesive backing, which are attached to the human subject as shown in FIG. 3. Two outer electrodes are connected to a constant current oscillator which provides 4 mA rms current with 100 kHz frequency. Any other arrangement of frequency and current and/or electrodes can be used which is, similarly, well above any known limits for physiological effects, but low enough to avoid the "skin" effects. The two inner electrodes, one of which is placed at the level of the xiphisternal joint, measure the transthoracic impedance. The output from the cardiograph are two analog signals (voltages) proportional to the electrical impedance, one representing $Z_O$ in ohms and the other dZ/dt in ohms/s. The conductance (impedance) can be continuously measured using this technique.

Figure 4:
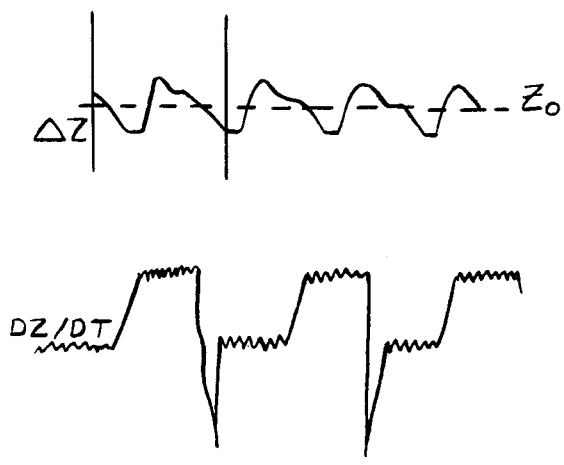
FIG. 4 is a graph plotting impedance signal (as measured in FIG. 3) against time.

Referring to FIG. 4, typical outputs of the plethysmograph are shown. These signals, dZ/dt, and ΔZ, provide all that is needed, in addition to the blood pressure measurements, to determine $R_i$ (measure the variation of areas of arterial lumens in the section of the body under consideration) since:

$$A(t) = \rho_e L G_e(t) \tag{8A}$$

and:

$$dA(t) = \rho_e L dG_e(t) \tag{8B}$$

Because L is the fixed, constant distance between the measuring electrodes, and $\rho_e$ may be assumed to have a fixed, time-independent value for a given patient. $R_i(t)$ is found from equation (8B):

$$R_i(t) = (e\, L G_e(t)/\pi)^{0.5} \tag{9}$$

Hence, the direct monitoring of the time variation of electrical conductance $G_e(t)$ (or impedance $Z(t)$) leads to the continuous monitoring of the time variation of the inner diameters of blood vessels. As pointed out in the preceding section, the simultaneous monitoring of $R_i(t)$ and $P(t)$, in combination with equation (9), provides all the information necessary for the determination of the unknown parameters (K, E and a) of the mathematical model.

Once the originally unknown parameters ($R_i(t)$, K, E and a) are determined, the integration of Equation (1) yields $v_z(t)$, which in turn yields the instantaneous flow $q(t)$:

$$q(t) = v_z(t) \times A(t)\ (CM^3/sec) \tag{10}$$

The flow Q of blood for any given time T is $$Q = \int_0^T q(t)\, dt\ (CM^3) \tag{11}$$

As soon as the link between the conductance measurements, (and thus $R_i$), pressure measurements, and hemodynamic equations is accomplished, the system is determined and can be solved for any or all hemodynamic parameters which are of interest. EHD is thus capable of measuring flow, vascular resistance, energy of the flow at any chosen section of the body, useful work or power of the heart and elastic properties of arterial walls as a function of pressure. By inputting the height and weight values of the patient, cardiac index and cardiac power index are also determinable. The rate of energy production of the heart provides one way for evaluating contractility parameters.

From the hemodynamic response of the circulatory system and its mechanical characteristics determined by EHD, the contractile properties of the heart muscle are determinable from measured values. In this procedure, the heart is considered as the input generator which causes the specific hemodynamic response. Hence, extremely valuable information about the heart muscle is supplied by this technique.

Pattern recognition analysis of P, Z and dZ/dt measured signals provides indications of disease states which can be quantified and displayed as additional hemodynamic characteristics. Thus, for example, the effects of drugs on disease can be monitored and displayed.

Referring to FIG. 5, a system embodiment of the present invention is shown. A plethysmograph 15 or other means for measuring and determining cross-sectional area, is coupled across a section of the patient's body 16. In the illustrated embodiment, the plethysmograph 15 is connected to electrodes 10, 11, 12 and 13. The two outer electrodes 10 and 11 are connected to a constant current oscillator which injects a signal across the section of the body being measured. The two inner electrodes 12 and 13 measure the impedance across the section of the body being measured, the transthoracic impedance in the illustrated embodiment. The plethysmograph 15 outputs two analog signals (voltages), one representing $Z_O$ in Ohms and the other dZ/dt in ohm/sec. The analog signals are output from the plethysmograph 15 via connection 19 to a processor 20. The processor 20 includes a central processing unit, such as a PDP11/03 minicomputer, or other minicomputer, or microprocessor, or discrete logic based computational and data processing unit. The analog signal output from the plethysmograph 15 to the processor 20 via connection 19 is coupled to the inputs of two input channels of an analog to digital (a/d) converter which forms a part of the processor 20. The processor 20 (integrally or peripherally) includes means for sampling the two a to d (A/D) converter channels a plurality of times during a fixed time period. The sampling may be done responsive to a computer program controlling the processor operation, or may be implemented in discrete logic, or by other appropriate means. In one embodiment, the two A/D converter channels are each sampled one hundred times per second during the period of one minute. The processor 20 further includes means for detecting the minimum value of the sample dZ/dt signal for each cardiac cycle, and for storing the detected minimum dZ/dt signal in an array. This may be done by means of a pattern recognition software routine of a computer program, or may be implemented directly in electronic logic. Additionally, the processor has means for sampling the value of $Z_O$ continuously over a period of time, and determining an average value for $Z_O$. This may be done via a software routine, or may be implemented in hardware. In one embodiment, sampling is done for one minute of values of $Z_O$, and an average value of $Z_O$ computed from the plurality of samples. After the average values of $Z_O$ and (dZ/dt)min are determined, they are displayed, such as via a video terminal, print-out, or other audio or visual means, either as discrete values, or as a curve or graph.

In accordance with the present invention, the illustrated embodiment of FIG. 5 further includes means for measuring blood pressure, shown as a band 18 extending about the arm of the patient 16. The blood pressure measuring means outputs an electrical signal via connection 21 to the processor 20. Alternatively, other means for measuring blood pressure may be provided, and the measurement of pressure may be on a scale of any kind, with the resultant signal being converted to an electrical signal compatible to and fed to the processor 20. An operator input device 25 is also coupled to the processor 20. Personal data about the patients under test is input via operator input device 25. Personal data may include such things as the age, height, weight, sex, and race of the patient under test, as well as the spacing distance between the measuring electrodes 10–13, and data such as the viscosity and resistivity of blood (as may be determined from the hematocrit determined from a blood sample). The processor 20, utilizing the techniques of the present invention and the formulas from the resulting model, determines desired hemodynamic characteristics in accordance with the input personal data, the blood pressure measurements, and the impedance measurement values. Signals representative of desired hemodynamic characteristics are output from the processor 20 to a means for displaying 40. The means for displaying 40 can comprise a printer, a video display, a chart recorder, or other visual or audio indication means. Exemplary hemodynamic characteristics which can be determined and displayed include the power of the heart, systemic vascular resistance, cardiac output, stroke volume, modulus of elasticity, cross-sectional area of blood vessels, kinetic energy of blood flow, pressure differential, blood pressure, systemic vascular flow, cardiac index, mean of stroke volume, rate of blood flow, total power per body surface area, as well as others. The system can provide an instantaneous value determination, or can determine time averaged maximum, minimum and mean values, or can determine absolute maximum and minimum values. Additionally, the system can determine values in terms of absolute, range, relative, deviation from mean, rate of change, etc. This flexibility is very important. For example, instantaneous readings allow for monitoring the effects of drug or gravity induced loading and unloading of the heart. By comparison to empirically determined norms, additional hemodynamic characteristics could be determined.

Referring to FIG. 6, curves Z and P are plotted against time, representing the impedance input Z and pressure input P to the processor 20 of FIG. 4. The curves represent the measured values, measured across a section of a living body over a certain time period, such as three or four cardiac cycles. The Z and P curves are plotted against a common time axis, such that the time correlation of the Z and P measurements may be seen as the points of intersection along a vertical line with the Z and P curves. For example, lines 30, 31, and 32, intersect the Z curve and P curve respectively, at corresponding times, such that Z1 and P1, Z2 and P2, and Z3 and P3 represent simultaneous measurements, respectively, of impedance and blood pressure. The curves also indicate the continuity of the measurements.

In accordance with the present invention, the modulus of elasticity of the blood vessel walls, as well as the cross-sectional area "A" of blood vessels in a section of a living body are determinable from three successive simultaneously measured pairs of Z and P samples, or from two simultaneously measured pairs of Z and P samples plus a calculated P value.

The measured impedance Z is related to the impedance of the tissue $Z_C$ and the impedance variation due to blood $\xi$ as $$1/Z = 1/Z_C + 1/\xi \quad (12)$$

$$\xi = \frac{\rho L}{A} \quad (13)$$

where $\rho$ is the resistivity of the blood (either an assumed value or a value determined from a measured blood sample (hemotocrit), L is the measured distance between the inner electrodes on the patient which are used to measure Z, and A is the cross sectional area of the blood vessel (or artery) within the section across which impedance is measured.

Substituting for $\xi$ in equation 12 as per equation 13 and solving for A yields $$A = \rho L \left( \frac{1}{Z} - \frac{1}{Z_C} \right) \quad (14)$$

A well known relationship for theory of elasticity states that $$A = A_o \left( \frac{P}{\left( \frac{K^2-1}{K^2+1} \right) E} + 1 \right)^2 = A_o \left( \frac{P}{E'} + 1 \right)^2 \quad (15)$$

where $A_o$ is the unstretched cross sectional area of blood vessel, and $k = R_o/R_i$ as defined above, and where $E' = [(K^2-1)/(K^2+1)]E$.

Combining equations 14 and 15 yields $$A = \rho L \left( \frac{1}{Z} - \frac{1}{Z_c} \right) = A_o \left( 1 + \frac{P}{E'} \right)^2 \quad (16)$$

$$A_{mean} = \rho L \left( \frac{1}{Z_o} - \frac{1}{Z_c} \right) = A_o \left( 1 + \frac{P_m}{E'} \right)^2 \quad (17)$$

The systolic pressure $P_S$ corresponds to the highest pressure, largest area and smallest impedance, Z min.

$$A_{max} = \rho L \left( \frac{1}{Z_{min.}} - \frac{1}{Z_c} \right) = A_o \left( \frac{P_s}{E'} + 1 \right)^2 \quad (18)$$

The diastolic pressure $P_d$ corresponds to the lowest pressure, smallest area, and largest impedance Zmax $$A_{min} = \rho L \left( \frac{1}{z\,max.} - \frac{1}{zc} \right) = A_o \left( \frac{P_d}{E'} + 1 \right)^2 \quad (19)$$

The mean (average of samples) pressure $P_m$ corresponds to the average impedance $Z_O$. For pairs of simultaneously measured (and averaged) samples, where $P_1 = P_s$ then $Z_1 = Z$ min, \quad (20)

where $P_2 = P_m$ then $Z_2 = Z_O$, and \quad (21)

where $P_3 = P_d$ then $Z_3 = Z$ max. \quad (22)

As shown with reference to FIG. 1,

A max = $A_1$ when $P_1 = P_s$, and $Z_1 = Z$ min \quad (23)

A mean = $A_2$ when $P_2 = P_m$, and $Z_2 = Z_O$; \quad (24)

A min = $A_3$ when $P_3 = P_d$, and $Z_3 = Z$ max. \quad (25)

By taking the ratios of the differences of the areas, each area term may be replaced by the inverse of the respective measured impedance term.

$$N_1 = \frac{a_2 - a_1}{a_3 - a_1} = \frac{\frac{1}{Z_2} - \frac{1}{Z_1}}{\frac{1}{Z_3} - \frac{1}{Z_1}} = \frac{Z_1 - Z_2}{Z_1 - Z_3} \cdot \frac{Z_3}{Z_2} \quad (26)$$

$$1/N_2 = \frac{a_1 - a_2}{a_3 - a_2} = \frac{\frac{1}{Z_1} - \frac{1}{Z_2}}{\frac{1}{Z_3} - \frac{1}{Z_2}} = \frac{Z_2 - Z_1}{Z_2 - Z_3} \cdot \frac{Z_3}{Z_1} \quad (27)$$

$$N_3 = \frac{a_1 - a_3}{a_2 - a_3} = \frac{\frac{1}{Z_1} - \frac{1}{Z_3}}{\frac{1}{Z_2} - \frac{1}{Z_3}} = \frac{Z_3 - Z_1}{Z_3 - Z_2} \cdot \frac{Z_2}{Z_1} \quad (28)$$

The ratios cancel the $\tau L$ portion of equation 14, and the differences cancel the two $1/Z_c$ components of equation 14.

Utilizing equation 16 to replace the Z components in equations 26, 27 and 28, $N_1$, $N_2$, and $N_3$ can be expressed in terms of $P_1$, $P_2$ and $P_3$ and $E'$.

$$N_1 = \frac{\left(\frac{P_2}{E'} + 1\right)^2 - \left(\frac{P_1}{E'} + 1\right)^2}{\left(\frac{P_3}{E'} + 1\right)^2 - \left(\frac{P_1}{E'} + 1\right)^2} \quad (29)$$

Solving equation 29 for E yields:

$$E' = \frac{1}{2} \frac{P_2^2 - P_1^2 + N_1(P_1^2 - P_3^2)}{P_2 - P_1 + \frac{1}{N_2}(P_3 - P_2)} \quad (30)$$

Solution for E' in terms of $N_1$, $P_1$, $P_2$, and $P_3$ may similarly be derived:

$$E' = \frac{1}{2} \frac{P_1^2 - P_2^2 + \frac{1}{N_2}(P_2^2 - P_3^2)}{P_2 - P_1 + \frac{1}{N_2}(P_3 - P_2)} \quad (31)$$

Solution for E' in terms of $N_3$, $P_1$, $P_2$, and $P_3$ may be similarly derived:

$$N_3 = \frac{\left(\frac{P_1}{E'} + 1\right)^2 - \left(\frac{P_3}{E'} + 1\right)^2}{\left(\frac{P_2}{E'} + 1\right)^2 - \left(\frac{P_3}{E'} + 1\right)^2} = \quad (32)$$

$$\frac{P_1^2 + 2P_1 E' - P_3^2 - 2P_3 E'}{P_2^2 + 2P_2 E' - P_3^2 - 2P_3 E'}$$

$$N_3(P_2^2 - P_3^2) + 2N_3 E'(P_2 - P_3) = P_1^2 - P_3^2 + 2E'(P_1 - P_3) \quad (33)$$

$$E' = \frac{1}{2} \frac{P_1^2 - P_3^2 + N_3(P_3^2 - P_2^2)}{P_3 - P_1 + N_3(P_2 - P_3)} \quad (34)$$

Substituting $P_s$, $P_m$, and $P_d$ for $P_1$, $P_2$, and $P_3$, respectively, according to the relationship of equations 20, 21, 22 yields:

$$E' = \frac{1}{2} \frac{P_s^2 - P_d^2 + N_3(P_o^2 - P_m^2)}{P_d - P_s + N_3(P_m - P_d)} \quad (35)$$

Substituting for $Z_1$, $Z_2$ and $Z_3$ with Zmin, Zmean and Zmax, respectively, in equation 28, according to the corresponding relationship from equations 20, 21 and 22 yields:

$$N_3 = \frac{Z_{max} - Z_{min}}{Z_{max} - Z_o} \cdot \frac{Z_o}{Z_{min}} \quad (36)$$

Making similar substitutions in equation 27 from equations 20, 21 and 22 yields:

$$\frac{1}{N_1} = \frac{Z_{max} - Z_{min}}{Z_o - Z_{min}} \cdot \frac{Z_o}{Z_{max}} \quad (37)$$

Dividing the numerator and denominator of equation 30 by $N_1$ and substituting $P_s$, $P_m$, and $P_d$ for $P_1$, $P_2$, and $P_3$, respectively, according to equations 20, 21 and 22, respectively, yields:

$$E' = \frac{1}{2} \frac{P_s^2 - P_d^2 + \frac{1}{N_1}(P_m^2 - P_s^2)}{P_d - P_s + \frac{1}{N_1}(P_s - P_m)} \quad (38)$$

Substituting for $1/n$, from equation 37 into equation 38 yields a solution of E, elasticity, in terms of $P_s$, $P_d$, $P_m$, $Z_{max}$, $Z_o$, and $Z_{min}$, according to the relationship:

$$E' = \frac{1}{2} \frac{P_s^2 - P_d^2 + \left(\frac{Z_{max} - Z_{min}}{Z_o - Z_{min}} \cdot \frac{Z_o}{Z_{max}}\right)(P_m^2 - P_s^2)}{P_d - P_s + \left(\frac{Z_{max} - Z_{min}}{Z_o - Z_{min}} \cdot \frac{Z_o}{Z_{max}}\right)(P_s - P_m)} \quad (39)$$

Taking the difference of equations 24 and 17 yields:

$$A_{max} - A_{mean} = \rho L \left(\frac{1}{Z_{min}} - \frac{1}{Z_c} - \frac{1}{Z_o} + \frac{1}{Z_c}\right) \quad (40A)$$

$$A_{max} - A_{mean} = \rho L \left(\frac{1}{Z_{min}} - \frac{1}{Z_o}\right) \quad (40B)$$

$$\rho L \left(\frac{1}{Z_{min}} - \frac{1}{Z_o}\right) = A_o \left[\left(\frac{P_s}{E'} + 1\right)^2 - \left(\frac{P_m}{E'} + 1\right)^2\right] \quad (40C)$$

Solving equation 40C for $A_o$ yields:

$$A_o = \rho L \frac{\frac{1}{Z_{min}} - \frac{1}{Z_o}}{\left(\frac{P_s}{E'} + 1\right)^2 - \left(\frac{P_m}{E'} + 1\right)^2} \quad (40D)$$

Solving equation 18 for $1/Z_c$ yields:

$$\frac{1}{Z_c} = \frac{1}{Z_{min}} - \frac{A_o}{\rho L}\left(\frac{P_s}{E'} + 1\right)^2 \quad (41)$$

Substituting for "$A_o$" from equation 40D into equation 41 yields:

$$\frac{1}{Z_o} = \frac{1}{Z_{min}} - \frac{\frac{1}{Z_{min}} - \frac{1}{Z_o}}{\left(\frac{P_s}{E'} + 1\right)^2 - \left(\frac{P_m}{E'} + 1\right)^2}\left(\frac{P_s}{E'} + 1\right)^2 \quad (42)$$

Proceeding in the same manner as just described, but taking the difference of equation 19 and equation 18 and solving for $1/Z_c$ yields:

$$1/Z_c = \left[\frac{Z_{min}}{\left(\frac{P_d}{E'} + 1\right)^2} - \frac{Z_{max}}{\left(\frac{P_s}{E'} + 1\right)^2}\right] / \quad (43a)$$

$$\left[Z_{max}Z_{min}\left(\frac{1}{\left(\frac{P_d}{E'} + 1\right)^2} - \frac{1}{\left(\frac{P_s}{E'} + 1\right)^2}\right)\right]$$

$$= 1/Z_{max}\left(\frac{P_s}{E'} + 1\right)^2 - 1/Z_{min}\left(\frac{P_d}{E'} + 1\right)^2 + \quad (43b)$$

$$\frac{1}{Z_{min}}\left(\frac{P_s}{E'} + 1\right)^2 - \frac{1}{Z_{min}}\left(\frac{P_s}{E'} + 1\right)^2$$

$$= 1/Z_{min} - \quad (43c)$$

$$\left[\frac{\frac{1}{Z_{min}} - \frac{1}{Z_{max}}}{\left(\frac{P_s}{E'} + 1\right)^2 - \left(\frac{P_d}{E'} + 1\right)^2}\right]\left(\frac{P_s}{E'} + 1\right)^2$$

Either of equations 42 or 43 yields a solution for $1/Z_c$ in terms of measured values and values computed therefrom, (eq. $Z_{min}$, $Z_o$, $P_s$, $P_m$ and E' for equation 42 and $Z_{max}$, $Z_{min}$, $P_s$, $P_d$ and E' for equation 43).

Having now solved for E' and $Z_c$, $A_o$ can be found corresponding to measured Z and P values.

The value of $\rho$ is obtained from the blood sample of the patient, or by assuming a typical value of $\rho = 150$ ohm-cm. The value of L is obtained by measuring the shortest distance between the inner electrodes of the plethysmograph. Both the values of $\rho$ and L can be fed into the processor 20 by the operator, such as via input device 25.

With E', $A_o$, and $Z_c$ determined, the value of the cross-sectional area, A, at any instant of time can be obtained and displayed on the display device 40. This display can be digital or in the form of a curve which is changing with time. This value is obtained by the use of either of equations 28 or 29 either in the form of a computer program utilized in conjunction with processor 20, or as embodied in hardware (electronic circuits) as processor 20.

The blood flow Q is set forth in equation 11. Alternatively, the blood flow Q can be determined as a function of the average blood pressure drop $\Delta P$, along the blood vessel of radius r and length L, and the area A as follows. The instantaneous flow through a section of the blood vessel is $$Q = \frac{A^2 \Delta P}{8\pi L \eta} \quad (44)$$

where $\eta$ is dynamic viscosity of blood previously determined, and $\Delta P$ is the average blood pressure drop along the blood vessel; also measured beforehand, or obtained from the following formula $$\Delta P = C/\sigma(A_{max} + A_{min}) \quad (45)$$

where $C = 0.25126x\ E^{0.5}$ \quad (46)

where $\nu$ is kinematic viscosity of blood measured beforehand, $A_{min}$ and $A_{max}$ are respectively the smallest and largest values of A (area) as derived from measured values during the cardiac cycle.

The values of $\eta$ and $\nu$ are either measured from the blood sample of the patient, or by assuming respective typical values. These values are fed into the processor 20 by the operator, such as by operator input means 25.

The cardiac output, CO, is derived by integrating Q over a one-minute period according to the following formula:

$$CO = \int_0^{1\ min.} Q dt, \text{ in cm}^3/\text{min} \quad (48)$$

Stroke volume, SV, is derived from CO according to the following relationship:

$$SV = \frac{CO}{\text{pulse rate}} \quad (49)$$

where the pulse rate is measured on the patient, and entered into the processor 20 by the operator such as via input means 25, or can alternatively be a directly coupled signal from the pulse rate measuring device to the processor 20.

Systemic vascular resistance, SVR, is a function of cardiac output CO and the average pressure drop (mean arterial—left arterial), and is derived according to the following relationship:

$$SVR = (P_m - 4\ \text{mmHg}) \times \frac{80,000}{CO} \quad (50)$$

where 4 mmHg is an approximation of left arterial pressure and the factor 80,000 adjusts units for compatibility of mmHg and Cgs (centimeter-gram-second) systems. The useful work of the left ventricle is defined as the work required to generate the potential energy of blood pressure and the kinetic energy of the blood. Since the work is a cumulative quantity (it is proportional to the time interval over which the flow is measured), it is better to use power instead of work. Power is defined as work done in one second.

The potential power of the heart (potential energy of building blood pressure and deforming vessel walls), POWP, and the kinetic powers of the heart (kinetic energy of blood pressure), POWK, are derived according to the relationship:

$$POWP = \frac{1332}{60} \int_0^{60\text{ sec.}} Q(Pm - 4)dt \quad (51)$$

$$POWK = \frac{0.529}{60} \int_0^{60\text{ sec.}} Q^3/A_{mean}^2 \quad (52)$$

The total power output of the heart, POW, is derived according to the relationship:

$$POW = \frac{POWP + POWK}{10,000,000}, \text{ where } 10,000,000 \quad (53)$$

is a unit adjustment factor.

Many more useful hemodynamic characteristics can be derived from those already derived. The mean of stroke volume (mean velocity of blood) is:

$$VMEAN = Q/A_{mean} \quad (54)$$

The kinetic energy of blood POWK can now be expressed in alternate terms from those of equation 52, as:

$$POWK = VMEAN^2 \, xQ \, X(0.529) \quad (55)$$

By measuring and deriving the mean arterial pressure PAMHG (measured or approximated) and measuring or assigning a value for right arterial pressure means RAPM (can be assigned a constant value such as 4 mmHg the average for a normal human adult population, or can be invasively measured using a catheter), the pressure differential PDIF can be expressed and displayed according to the relationship:

$$PDIF = PAMHG - RAPM \quad (56)$$

The power value POWP, can be alternatively expressed (from that of equation (51)) as:

$$POWP = PDIF \times Q \times M. \quad (57)$$

where M=1332 for the illustrated embodiment.

Total power is still expressed as in equation 53, with POWP being obtained from equation 51 or 57, and with POWK being obtained from equation 52 or 55.

By measuring and deriving the body surface area (BSA), and inputting BSA (or the height and weight of the patient) into the processor 20, such as by input means 25, the cardiac index (CI) can be expressed and displayed according to the relationship:

$$CI = CO/BSA \quad (58)$$

By measuring heart rate (HR) and inputting HR into the processor 20, such as automatically or manually via input means 25, the stroke volume SV representing the amount of blood ejected during a single contraction of the left ventricle can be expressed and displayed according to the relationship:

$$SV = CO/HR \text{ (per minute since CO is expressed per minute).} \quad (59)$$

Systemic Vascular Resistance can be alternatively derived as:

$$SVR = PDIF \times N/CO, \quad (60)$$

where N=unit adjustment factor, e.g. N=80,000 for one embodiment.

The cardiac power index CPI provides a normalized value of cardiac power (referencing POW to BSA) according to the relationship:

$$CPI = POW/BSA. \quad (61)$$

The work, WRK, done by the heart in t seconds is $$WRK = POW \times t \quad (62)$$

Thus, to determine the work per minute, t=60.

In addition to the many alternative techniques already described (such as equations 30, 31, 34 or 35), or referred to, for deriving E and E' from P and Z measurements, E' can also be determined in accordance with the following relationships:

$$E' = B \times R \quad (63)$$

$$\text{where } B = \frac{P_1 - P_3}{\sqrt{M} - 1} \quad (64)$$

$$\text{and } M = \frac{Z_2 - Z_3}{Z_2 - Z_1} \cdot \frac{Z_1}{Z_3} \quad (65)$$

$$\text{and } R = D + F \times Z_2 \quad (66)$$

and D and F are constant numbers, experimentally determined to have values D=0.7254456, F=0.00458779.

The remainder of the derivations of hemodynamic characteristics follows the same techniques disclosed herein, above.

Alternatively, numerous other derivational techniques may be utilized to achieve the same results.

Referring to FIGS. 7–8, the section of the blood vessel being measured is shown, for diastole (FIG. 7A) and systole (FIG. 7B). The systolic blood pressure $P_S$ arises when the heart pumps, diastolic pressure when the heart is at rest. When the heart pumps, the blood flows through the vessel with maximum velocity and pressure ($P_S$) and the blood vessel is stretched to its maximum area ($A_{max}$) (FIG. 8). When the heart is at rest, the blood flows through the vessel with minimum velocity and pressure ($P_d$) and the blood vessel, having elastic properties, resiliently returns to its minimum area ($A_{min}$) (FIG. 8).

Referring to FIG. 8, the blood vessel of FIGS. 7A–B are shown in cross-section, illustrating the correspondence of $P_S$ to $A_{max}$, $P_d$ to $A_{min}$, and $P_{mean}$ (an average derived from a plurality of pressure measurements during a cardiac cycle) to $A_{mean}$.

Referring to FIG. 9, the interrelationships of P to Z to A are shown plotted on a 3-axis graph.

The measured impedance Z is inversely proportional to the cross-sectional area of the section of the blood vessel across which the measurement is made. From FIG. 9 it is seen that $$P_d \rightarrow Z_{max} \rightarrow A_{min} \quad (67)$$

$$P_S \rightarrow Z_{min} \rightarrow A_{max} \quad (68)$$

$$P_{mean} \rightarrow Z_{base} \rightarrow A_{mean}, \text{ where } Z_{base} = Z_0 \quad (69)$$

Referring to FIG. 10, an electrical block diagram of a processor based system embodiment of the present invention determining hemodynamic characteristics is shown.

In the illustrated embodiment, a bioimpedance measurement system is utilized to provide measurements of the impedance Z ($Z_O$, $\Delta Z$, and $dZ/dt$) across a section of the body. The impedance measurement device 100 manufactured may be of any type, such as the commercial bioimpedance instrument BR 100 by Beckman Instruments. A plurality of wires 101 are coupled from the measurement device 100 to electrodes which are placed across the section of the patient's body under test. The output from the electrodes are coupled via wires 101 to the impedance measurement device 100, which outputs signals indicative of impedance measurements onto a common bus 111. Additionally, a communications link 102 couples the impedance measurement device 100 and a processor 120. In the illustrated embodiment of FIG. 10, a commercial multi-bus based processor system was chosen, such as is available from Intel. In the illustrated embodiment, the processor 120 is multi-bus compatible board, such as containing an 8080 or, 8085, 8011, Z80 or other processor based bus compatible processing board. While the description of FIG. 10 will hereafter refer to the particular configuration utilizing multi-bus compatible boards, any equivalent functional system, whether or not multi-bus compatible, may be used to effectuate the present invention. Alternatively the present invention may be embodied without the use of digital processors, and may be implemented directly in electronic hardware (logic).

An output of the impedance measurement device 100 is coupled to an analog to digitial (A/D) converter 105, with an output of the A/D 105 coupling to the bus 111. The A/D converter may be a custom design, or may be a standard commercially available product. The analog electrical signals representing impedance and change in impedance as output from the impedance measurement device 100 are coupled to the A/D converter 105 where these analog signals are converted to digital equivalent signals which are output to the bus 111 for utilization by the processor. User data, such as personal data about the patient, are entered into the processor, such as via a keyboard 128 or other types of input devices, while switches 126 provide selection means for the mode of the overall system, as well as the input mode. A display, such as light-emitting diodes 127, provides a visual indication (display) to the user of the status of the system. The switches 126, display 127, and keyboard 128 are interfaced to the bus 111 via an interface means 125. The interface 125 provides for compatibility, of signal levels and timing requirements, with the bus standard of the bus 111 (in the illustrated embodiment the multi-bus standard). Interface 125, as well as interfaces 165, 175 and 185, to be discussed infra, can be implemented with different bus standards could be unnecessary, depending on the common bus 111 to which the peripheral units are to be interfaced. In the illustrated embodiment, the data as input from the keyboard 128 and switches 126 are coupled via the bus 111 to the processor 120 for utilization in determining hemodynamic characteristics. A blood pressure unit 160, such as the Century blood pressure measurement system (which provides automatic indirect blood pressure oscillometric measurement of blood pressure utilizing a cup), is coupled to the patient under test and provides outputs indicative of measured blood pressure of the patient. The output of the blood pressure unit 160 is coupled to an interface 165 which transforms the outputs from the blood pressure unit 160 to signals compatible with the bus structure 111. In the illustrated embodiment, the blood pressure interface 165 performs a USART function (universal-synchronous-asynchronous-receiver-transmitter).

A nonvolatile memory 130 and a read-write memory 140 are coupled to the bus 111. The nonvolatile memory 130 may be read only memory (ROM), programmable read only memory (PROM), erasable programmable read only memory (EPROM or EEROM), or battery backed up volatile read-write memory. The nonvolatile memory 130 provides program storage which is utilized by the processor 120 to effectuate calibration, sampling of measurement data, determination of hemodynamic characteristics in accordance with the equations and theory as set forth herein above, and display of determined characteristics. For example, in one embodiment, 16 kilobytes of nonvolatile memory is utilized, though lesser or greater amounts of program storage will be required depending on the processor used, the programming language chosen, and the compactness of the coding. Alternatively, the nonvolatile memory 130 may be replaced with volatile memory such as read write memory, with or without battery backup, in which case the program data is down loaded into the memory 130 from a nonvolatile storage medium such as bubble memory, magnetic tape, disc, paper tape, etc. The read write memory 140 can be implemented in static RAM, dynamic RAM, clocked static RAM or pseudo-static (self-refreshing dynamic RAM), etc. The amount of read write memory 140 required is again dependent on the choice of processor type 120, as well as the programming language chosen, and the approach chosen to implement determination of hemodynamic characteristics. The nonvolatile memory 130 and read write memory 140 may be comprised of off the shelf purchased commercial boards compatible with the chosen bus structure, or may be customer custom semi-custom designed boards, according to the users needs. A power supply 150 provides power to the A/D converter 105, processor 120, interfaces 125, 165, 175, 185, memories 130, and 140, an optional time of day clock 190, and elsewhere in the system as required. For example, where other bus interface means are provided, the power supply provides appropriate power thereto also.

A display means 170, such as a printer, plotter, or video display, provides a visual indication of the determined hemodynamic characteristics, as well as providing capability for displaying intermediate terms and actual measurements. The processor 120 provides signals via the bus 111 to a display interface 175. The interface 175 transforms the signal from the bus 111 to a form compatible with the display means 170, and outputs the compatible signals from the interface 175 to the display means 170. Off-line data storage capability is provided by a nonvolatile storage means 180, such as a printer, or storage-retrieved means such as tape transport, disc drive, bubble memory, EPROM, etc. Data to be stored in the storage means is coupled via the bus 111 to an interface 185, which converts the format of the received data from the bus format of 111 to the nonvolatile storage means 180 compatible output format said output being coupled to the storage means 180. For example, where the storage means 180 is comprised of a magnetic tape storage means, the interface 185 performs modulation and demodulation back and forth between frequency modulated signals for storage on the tape and digital signals for storage or use with the digital subsystem (processor 120, memories 130, 140, etc.). In the illustrated embodiment, a time of day clock 190 is coupled to the bus 111 for communication of time of day information to the processor 120 and display interface 175. The time of day clock 190, storage means 180, interface 185, display means 170, and display interface 175 may be partially or totally replaced or deleted or added to, according to desired system performance criteria. The storage means 180 provides a method for data logging, that is tracking the measured data signals and storing in a real time basis the measurements for later use and analysis by the operator of the illustrated system.

In a system of FIG. 10, the processor 120 in accordance with stored program execution instructions from memory 130 and 140, through utilization of the equations as set forth above, and the pressure and impedance measurements from blood pressure unit 160 and impedance device 100, determines intermediate physical signals which are in turn utilized to deterine hemodynamic characterstics. The intermediate physical signals and finally determined characteristics can be displayed as data points, or as a curve, or can be converted back to analogue form for use or display by the system, corresponding to the physical system measurement intermediate term or hemodynamic characteristic, by use of a digital to analogue converter or the like. The sampled signals can be summed, averaged, minimum and maximum peak detected, and/or otherwise operated upon, and the base sampled values or operated on values (intermediate terms) can be utilized to determine selected hemodynamic characteristics. Either two sets of simultaneously measured pressure and impedance measurements may be used (e.g., $P_S(Z_{min})$, $P_d(Z_{max})$ referenced two point measurement) or three pairs of simultaneous pressure and impedance measurements can be used, (e.g., $P_S(Z_{min})$, $P_d(Z_{max})$ Pmean ($Z_O$) referenced — three point method) in accordance with the above described techniques to determine desired hemodynamic characteristics. Where the two point technique is utilized, the mean pressure (Pmean) is calculated and a correction factor is calculated (e.g., such as in the CREO program from the listing) to remove deficiencies occurring from linearization of the nonlinear model by which the two measured points are utilized to determine both the third point (Pmean) and the elasticity (E') (in its uncorrected form). With the three point measurement system, the mean pressure (Pmean) is determined from measured values, and no correction factor is required for E'.

The operation of the illustrated system of FIG. 10 can be functionally structured in four parts: calibration, sampling, calculation, and report generation. Other system operating structures are acceptable which provide functional equivalence to that set forth herein. Each of these functions shall be described in particular with reference to the illustrated embodiment of FIG. 10. The following description is meant to be illustrative, and not limiting In the calibrate mode, an impedance box within or coupled to the impedance measuring device 100 is activated. The impedance measuring device 100 provides two outputs to the A/D converter 105, an impedance signal Z, IADC(0), and a change in impedance with time signal dz/dt, IADC(1). The operator (or other appropriate person) first sets the calibration box to the ZO mode. The system of FIG. 9 then initializes variables, and samples IADC(0).

The digital output of the A/D converter 105 is IZ1 corresponding to IADC(0). IZ1 is stored in the read-write memory 140 for use by the processor 120 in accordance with the stored program instructions of the memory 130. Alternatively, the IZ1 value may be stored in flip-flops or in registers within the processor 120. The value IZ1 is adjusted for the analog voltage zero offset of each of the A/D converter channels 105 and the impedance measuring device 100, and the resultant signal, IZ0, is stored in read-write memory, either in the processor 120 in a register, or in the read-write memory 140. A plurality of IZ0 samples are taken, and averaged (sum of samples divided by number of samples) to determine a ZO mean calculated value (ZOMC).

Referring to FIG. 11, IZ1 corresponds to the input samples analog signal corresponding to the ZO measurement. IZ0 is the zero offset adjusted digital signal equivalent of IZ1. Z1 is the total sum of a plurality of IZ0 samples. ZOMC is the average of the IZ0 signals determined by dividing Z1 by the number of samples (MM)

$$ZOMC = Z1/MM \tag{71}$$

In the calibrate ZO mode, the IADC(0) signal output is 25 OHMS, corresponding to ZO equal to 25 Ohms calibration. Additionally, in the calibrate Z0 mode, the IADC(1) signal is equal to zero ohms per second corresponding to calibration of DZ/DT equal to zero.

The next step in the calibration process is comprised of setting the impedance calibration box to the DZ/DT mode. In this mode the signals measured by the impedance device 100 and converted by the converter 105 correspond to IADC(0) = Z0 = 0 Ohms as output from the calibration box. The sampled calibrated signal is defined as IZ2, as shown in FIG. 11. Additionally, a dZ/dt mode IADC(1) signal is output and corresponds to DZ/DT = 0.1 ohms per second, and is designated as IDZ2, as shown in FIGS. 12-13. The processor inputs signals from both channels of A/D 105 and determine an average value of IADC(1) above a predefined threshold as CRT = SUM/K where SUM = the sum of values of dZ/dt above the threshold, and KK = the number of samples in SUM as shown in FIG. 13. The value CRT determines the thresholds above and below which independent sums are formed as discussed below, and as shown. In accordance with the illustrated embodiment of FIG. 10, and as illustrated in FIGS. 12, 13, and 14, the processor 120, in accordance with stored program instructions from the memories 130 and 140, inputs the digital signals IZ2 and IDZ2, and adjusts these signals for the zero offsets (and/or other factors) of the sampling device 100 and A/D converter 105. The offset adjusted signals resulting are Z02 and DZ2 corresponding to the IZ2 and signals, respectively.

The Z02 adjusted digital samples of the measured ZO impedance values are summed together and stored as the variable Z, as shown in FIG. 14. The number of Z02 samples in the sum Z is counted and stored as the variable KZ. The average of the Z02 samples is computed by dividing Z to KZ to determine ZEROZ. ZEROZ represents the average of the zero offset adjusted IADC zero samples for the ZO=0 calibration (DZ/DT calibrate mode). The ZO mean value (ZOM) is determined as the differential of the determined average of the zero offset adjusted IADC(0) average ZO value [for ZO equals 25 ohms (ZO calibrate mode)] (ZOMC), less the determined average of the zero offset adjusted IADC(0) [for ZO equals 0 Ohms (DZ/DT calibrate mode) (ZEROZ). That is, $$ZOM = ZOMC - ZEROZ \qquad (72)$$

The ZOM value may be adjusted to compensate for measuring instrument calibration scale. For example, the calibrated ZOM value (CZ)=ZOM x the adjustment factor, or as shown in FIG. 13 ZOM divided by 40 equals CZ for the illustrated embodiment of FIG. 10 with the above described equipment utilization.

Referring again to FIGS. 12 and 13 the utilization of the DZ2 (offset adjusted IADC(1) signal) closely follows the technique used with reference to FIG. 14. However, with reference to DZ2, both a zero level DZ (ZRODZ) and a mean calculated value of DZ (DZMC) are determined from the measured DZ2 values. A plurality of DZ2 samples are taken and input to the system. The DZ2 samples are first separated into two groups, and DZ2 values within each group are summed together. First, DZ2 samples which have a value greater than the CRT value (as determined and discussed with reference to FIGS. 12 and 13 are summed to form a variable DZ. The number of samples in the sum DZ are counted and stored as variable LL. The mean calculated value for DZ and the DZ/DT calibrate mode for values greater than CRT (DZMC) is calculated by dividing the sum DZ by the number of samples LL, or expressed in equation form $$DZMC = DZ/LL \qquad (73)$$

as shown in FIG. 12. Thus, DZ represents the sum of all values above the threshold of CRT, and DZMC represents the average (mean) value of DZ2 samples above CRT threshold level. Additionally, all DZ2 samples less than or equal to seven and greater than are equal to minus thirty are summed together to form the variable DZDTS. DZDTS represents the total sum of zero level threshold DZ2 samples. The number of DZ2 samples summed to form DZDTS is counted and stored as variable LDZ0, and the calibrated average 0 level 0 offset adjusted DZ/DT zero level signal is determined as $$ZRODZ = DZDTS/LDZ0 \qquad (74)$$

The differential of the averaged values DZMC and ZRODC, representing averages for the two threshold levels for summation, can be used for determination of the calibration adjustment for DZ. DZ mean (DZM) is calculated as $$DZM = DZMC - ZRODZ \qquad (75)$$

The physical relationship of DZ2, CRT, DZMC, ZRODZ, and DZM can be clearly seen by reference to FIG. 12.

This completes the calibrate function for the illustrated embodiment, and other embodiments of the calibrate function can be utilized in accordance with the mandates of the system. The next function the system must perform is the sample function.

In the illustrated embodiment, the sample function is embodied in a processor coordinated sampling and array establishment, and some simple manipulations of sample data to determine intermediate terms required for the calculate function. Alternatively, all calculations may be deferred, or all calculations may be included within the sampling function. The functions to be performed by the sampling portion function of the system will be somewhat controlled by the timing requirements imposed by the system sampling rate and the instruction cycle time requirements of the processor 120. With this understanding, the following discussion of the illustrated embodiment is meant as illustrative, and not as limiting.

The sample function in the illustrated first initializes variables and sets up necessarily constants. The system has been switched from the calibrate mode to the sampling mode prior to commencement of the sampling function. This may be effectuated by an operator actuating a switch, or may be automatically commenced responsive to program control of the system itself. The IADC(0) signal is sampled (the ZO output is sampled), and assigned a value IZ00. Next, the sampled input is adjusted to account for the average Z0 calibration and for the offset of the measuring instruments, the adjusted value assigned the lable IZO.

$$IZO = IZOO - ZEROZ - 2048 \qquad (76)$$

similarly, the IADC1 output (corresponding to DZ/DT input) is sampled and is assigned a label IDZ1. IDZ1 is then adjusted for the average 0 DZ/DT calibration and the 0 offset adjustment of the measuring instruments, and is assigned a label IDZ.

$$IDZ = IDZI - ZRODZ - 2048 \qquad (77)$$

The present value of IDZ is there assigned a value DZJ = −IDZ, to account for the inverting nature of the measuring instrument. Additionally, a label DZI=DZJ is established, with DZI being utilized during the next sample period to represent the previous sample value of DZJ. Arrays are set up for IZ0, IDZ, DZJ, DZI, and other values such as the count of the number of positive IDZ samples, KPK, the maximum IDZ value for each sample cycle, MXDZ, sums of the measured signals, maximum values of each sample cycle for the measured signals, and minimums of the measured signals. MXDZ is determined according to the relationship: if IDZ is greater than the current MXDZ, then MXDZ=IDZ. Integration is accomplished, in part, by summing the previous IDZ sample DZI with the present IDZ sample (DZJ) to form the summed value. After this, the present IDZ is assigned as the previous IDZ sample, or an equation form DZI=DZJ. The relationships between DZI, DZJ, and DZIO (the previous DZJ sample), to the determination of SDZ is more clearly seen by reference to FIG. 16. The relation of IADC1 to IDZ1, and of DZJ to IDZ and DZI, and the relationship of IDZ1 and IDZ2 to DZDTZ is shown in FIG. 15.

Figure 17:
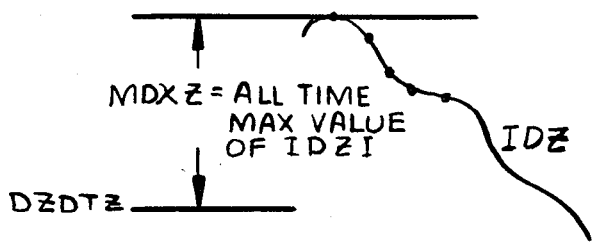

Referring again to FIG. 16, and to the discussion of the sample function, the sum SDZ can be adjusted in numerous ways to derive intermediate terms for use by the calculate function. For example, an adjustment factor, YD, can be added to SDZ to determine an intermediate adjusted sum value ZD, where $ZD = SDZ + YD$. All of the sampled ZD may be summed, and adjustment factor SZ0 added, to determine an intermediate term SZ, where $SZ = SZ + ZD + SZ0$. The sum of the SZ values can be determined, adding an appropriate adjustment factor, to determine a value SZ, where the intermediate term $HSZ = HSZ + ZD + HSZ0$. The relationship of ZD, SZ, and HSZ, and adjustment factors YD, SZ0, and HSZ0, can be clearly seen from FIG. 16. The relation of MXDZ to IDZ and IDZ1, and to DZDTZ can be more clearly seen by reference to FIG. 17.

Figure 18:
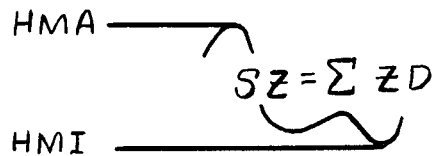
Figure 19:
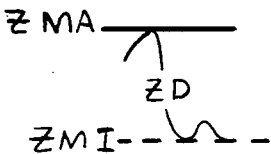

Referring to FIG. 18, additional features may be implemented in the sample function. For example, a maximum SZ value HMA per sample cycle can be established, according to the relationship if SZ is greater than HMA, then SZ=HMA. Similarly, a minimum SZ value HMI per sample cycle can be established according to the relationship where if SZ is less than HMI then SZ=HMI. Similarly, terms for the maximum ZD value per sample cycle ZMA, and the minimum ZD value per sample cycle, ZMI, may be established according to the relationships where if ZD is greater than ZMA, than ZD=ZMA and where if ZD is less than ZMI, then ZD=ZMI. The relationships of ZMA, ZMI, and ZD are seen more clearly from FIG. 19.

Figure 20:
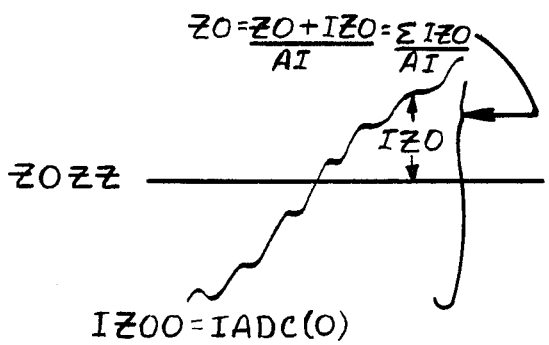
Figure 21:

In the illustrated embodiment, arrays are now established for each sample cycle for ZMA, ZMI, HMA, HMI, HSZF, HSZ, SZ, MXDZ, and count values of number of samples per sample cycle, such as BI, and KPK. After each sample cycle, a test is made for completion of sampling. When a predefined number of sample cycles has been completed, the testing is deemed completed, and the A/D converter 105 ceases transmission of information to the processor 120. The determination of ZD, SZ, and HSZ are adjustments to compensate for impurities introduced in the IDZ signal from the DZ/DT sample, caused by the sampling device 100, A-D converter 105, and any electronic filtering utilized. These adjustments restore the IDZ sample, by integration, to the desired DZ/DT value. Once the actual sampling feature of the sampling function is completed, the sum values stored in the arrays are operated upon to calculate and determine intermediate values for use by the calculate function. The interrelationships of IZ00, IADC0, IZ0, Z0, and ZOZZ can be more clearly understood by reference to FIG. 20. The relationship of IDZ to MXDZ, and to MY(I) [the array variables storing each MXDZ for each cycle] is shown in FIG. 21.

Figure 22:
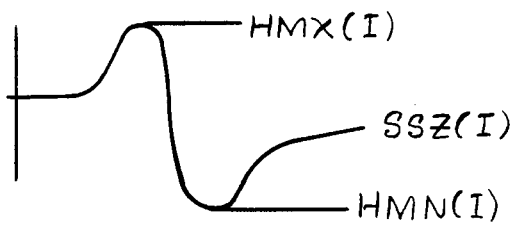

Referring to FIG. 22 the relationship of SZ to ZD, and of SZ to HMX(I) [the array variable stored for each sample cycle of the maximum SZ value for that cycle and to HMN(I) [the array variable stored for each sample cycle of the minimum SZ sample for that cycle], and to SSZ(I) [the array variable representing the SZ value for each sample cycle] are shown.

Figure 23:
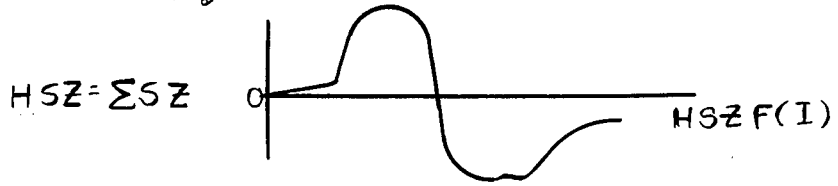

Referring to FIGS. 23, the interrelationship of HSZ to SZ and of HSZ to HSZF(I) is shown. HSZF(I) represents the array of values of HSZ, each value for each sample cycle stored in a different array element.

Figure 24B:
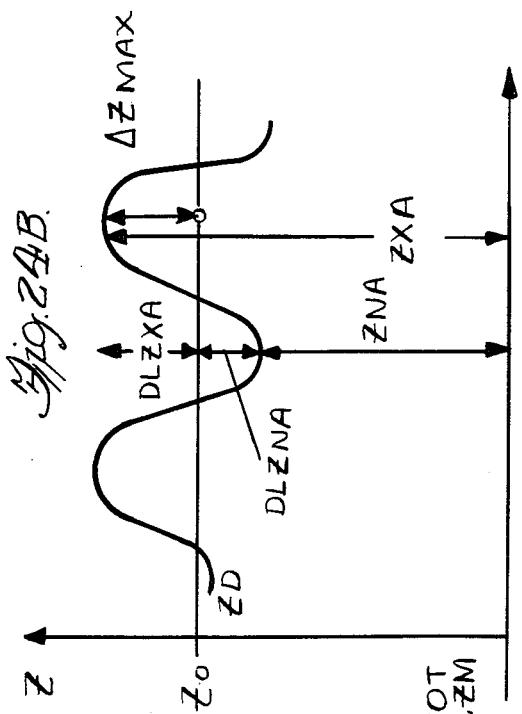
Figure 24A:
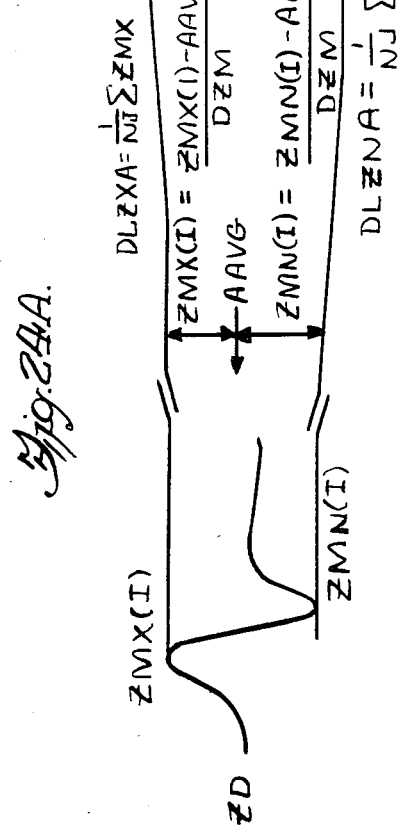

Referring to FIGS. 24A and B, the relationship of ZD to a number of determined intermediate values is shown. The maximum value of ZD per each sample cycle is stored in an array element of ZMX(I), and the minimum value of ZD per each sample cycle is stored in an array element of ZMN(I), as shown in FIG. 24A. As described above, ZD is the sum of DZJ samples which represents the inverted sum of the adjusted and calibrated IADC(1) for each sample cycle. An average value, AAVG for the sum of adjusted DZ/DT inputs represented by SZ, is determined for each sample cycle according to the relationship AAVG=SSG(I)/AJ(I), where AJ(I) is the number of samples in the sum SSZ(I). Utilizing AAVG as a base line, the values of ZMX(I) and ZMN(I) can be determined with reference to AAVG, according to the relationship $ZMX(I) = (ZMX(I) - AAVG) \times T/DZM$, where T is a sampling rate conversion constant, and DZM=a normalization constant previously determined in the calibrate function portion of the systems operation. In a similar matter, the minimum ZD value for each cycle referenced to AAVG and normalized for calibration, may be determined according to the relationship $ZMN(I) = -(AAVG) \times T/DZM$. The absolute maximum values of ZD, and absolute minimum values of ZD, can be determined in a number of alternate ways, as can most of the derivations described herein. For example, first, a sum of the maximum ZD values may be determined according to relationship $ZMXA = ZMXA + ZMX(I)$, and the sum of the minimum values of ZD's can be derived according to the relationship $ZMNA + ZMN(I)$. The average of the maximum ZD's, and the average of the minimum ZD's, can be determined according to the relationship DLZXA=ZMXA divided by NJ, where NJ=the number of samples utilized in determining the sum ZMXA, and the average minimum ZD can be determined according to the relationship DLZNA=ZMNA/NJ, where NJ is the number of samples utilized in determining the sum ZMNA. The maximum value of ZD, ZXA, and min. value of ZD, ZNA, as shown in FIG. 24B, can be determined according to the relationship $ZXA = Z0 + DLZXA =$ max. value, and $ZNA = Z0 + DLZNA$, where Z0 is previously determined as described above. The relationship of Z0, ZD, DOZXA, DOZNA, ZNA, ZNA, and ZXA, is shown in FIG. 24B. Other intermediate terms can also be derived. For example, the average of the MXDZ samples can be determined, as SumY, according to the relationship SumY=SumY+MY(I) [where MY(I)=the array of values of MXDZ]. The average MXDZ, as factored and adjusted for calibration, can be determined as TADZM, according to the relationship TADZM=SumY/NJ/DZM, where NJ=the number of samples summed in SumY, and DZM=a normalization constant as derived in the calibrate function. The differential of the determined average maximum to minimum ZD, DLZA, can be determined according to the relationship $DLZA = DLZXA - DLZNA$.

Elasticity E', can now be calculated. If the two point model is utilized, then a correction factor must be computed to compensate for deficiencies in linearization of the model. Utilization of the three point model eliminates the need for a correction factor.

Figure 25:
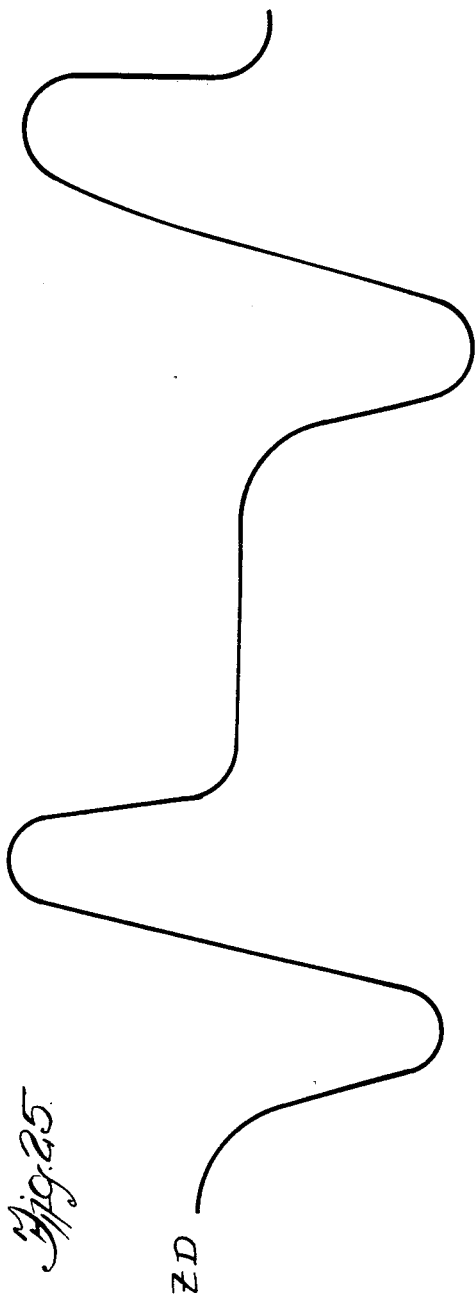

Referring to FIG. 25, a graph is shown of the ZD value for a plurality of sample cycles (i.e., plotted against time). Referring to FIG. 26, the relationship of the SZ value to time is shown, exhibiting the SZ signal value for plurality of sample cycles (i.e., plotted against time). Referring to FIG. 27, a graph plotting a typical value of HSZ verses time illustrating the HSZ signal value for plurality of sample cycles.

The $\xi$ terms N1, N2, and N3 corresponding to equation 26, 27 and 28, may now be determined from measured P and Z values and from intermediate terms derived to this point. Utilizing equations 37 through 40, N1 is first expressed in terms of the impedance measured and derived averaged values and base impedance value ZO, utilizing (in the illustrated embodiment) Z0, DLZXA, DLZNA, ZXA, to determine N1. Alternatively another N value and set of equations for corresponding E could be utilized. Additionally, utilizing the measured values of pressure ($P_S$, Pd), and the determined values Pm, ZO, and $Z_{max}$ and $Z_{min}$, the elasticity value E' is determined, such as by means of equations 38 and 39. The background impedance ZC can be determined from measured pressure values (Pd and $P_s$), derived elasticity value E', and ZNA and ZXA derived values (equations 41-43). The maximum and minimum cross sectional areas can then be determined from equations 16-19, utilizing ZXA, ZC, $\rho$ (resistivity), and L (distance between the measuring electrodes), or in terms of measured pressure ($P_s$ for Amax and $P_d$ for Amin), determined elasticity value E', and a determined value of A0. Furthermore, the mean area, $A_{mean}$ may be determined according to equation 17 with Z0 substituted for Z, or with $P_{mean}$ (average of samples) pressure (corresponding to average impedance ZO) substituting for P. The base area (unstretched area) of the blood vessel can be determined according to equation 40d, or may be alternatively derived a number of ways, such as deriving $A_o$ from equation 18 (given Amax, PS, and E'.) Additional features which may be performed either in the sample function or calculate function include determination of ratios of areas, differences and ratios of pressure and impedances and derivations from measured values of impedance and pressure, and compensation adjustments for pressure and impedance measurements and measurement derived values.

Where derivation of hemodynamic characteristics is based upon the two point measurement technique, the elasticity value determines, as in the manner described above with regard to the sample function, represents an unadjusted elasticity factor, which must be adjusted to compensate for the correction of deficiencies of linearization from a nonlinear model. As discussed above, utilization of the three point measurement technique eliminates the need for determination of a correction factor. Where the two point measurement technique is utilized, an additional function, CREO, can be utilized to calculate the adjustment factor. In utilizing the two point technique, the elasticity E' and intermediate terms necessary to determine E' are derived in a manner similar to that discussed above. First, constants and variables are initialized, such as C, D, REO1, REO2, etc. An adjustment factor is determined for the base line impedance component of DCT, according to the relationship $DCT = C + T \times Z0$. Next, the impedance of the tissue $Z_C$, representing the background impedance, is determined according to the relationship $ZC = Z0 + DCT$.

An unadjusted elasticity value, EPSO, may now be calculated in terms of ZC, ZNA, ZXA, PS, and PD. In the illustrated embodiment, first intermediate terms are derived according to the relationships $ZC1 = (ZC - ZNA)/(ZC - ZXA)$, $ZC2 = ZXA/ZNA$, $ZC1R = ZC1$, $ZC2R = ZX2$ and $EPSO = (PS - PD)/(ZC1R \times ZC2R - 1.0)$. EPSO represents an unadjusted elasticity value, since the value of EPSO has been determined in a linear fashion. The adjustment factor, REO, is determined selectively based on the value of Z0, in the illustrated embodiment. In the illustrated embodiment, if Z0 is greater than 18, ohms than REO equals $C + D \times Z0$, where C and D are constant values, and Z0 is a measured and determined parameter. If Z0 is less than or equal to 18 ohms, then REO1 equals a constant value (0.4163 . . . in the illustrated embodiment), and a warning is displayed that Z0 is too small. This warning notifies the operator that there is a probable error, or that the patient is in an unstable condition, or other problems. An adjusted elasticity value, EPSIL, represents the elasticity value E' as described hereinabove, according to the relationship $EPSIL = EPSO \times REO$.

Additionally, where the two point measurement technique is utilized, the determination of the value $Y_F$ used in the sample function is determined based upon the value of TADZM corresponding to value DZ/DT max value. If TADZM is greater than 1.8148 . . . , then $Y_F$ is equal to 1.62, in the illustrated embodiment for two point measurement technique. If TADZM is less than or equal to 1.8148 . . . , than $Y_F = (0.8031 - \times TADZM - 0.16245)$, in the illustrated embodiment. However, if TADZM is less than 0.7, then a display warning is given that DZ/DT is too small, in the illustrated embodiment for the two point measurement technique.

Additionally, where the two point measurement technique is utilized, the illustrated embodiment further includes within the REO function, the selection of constants for use in determining the correction factor YVF for determining cardiac output CO. Thus, if the patients sex is male, then three constants (e.g. VM0, VM1, VM2) are assigned a first set of values, whereas if the sex of the patient, is female, the three constants are assigned different values. Next, the correction YVF is determined in accordance with the selected values of VM0, VM1 and VM2, and the relationship $YVF = VM0 = VM1/TADZM = VM2/TADZM$.

It is again emphasized, that no correction factors are required where the three point measurement technique as disclosed herein is utilized instead of the two point measurement technique. Thus, the CREO function is not required for the three point measurement technique. However, regardless of whether the two or three point measurement technique is utilized, the next function of operation of the system is the calculating function.

The calculation function of the present system determines the desired hemodynamic characteristic based upon measured values and values determined from measured values. For example, values can be determined according to equations 44 to 66, for may be alternatively determined, or the instantaneous flow of blood through the blood vessel, Q, cardiac output, CO, stroke volume, SV, systemic vascular resistant, SVR, potential energy of blood flow, POWP, kinetic energy of blood flow, POWK, total power output heart, POW, mean of stroke volume, VMEAN, pressure differential, PDIF, cardiac index CI, stroke volume, SV, cardiac power index, CPI, work, WRK, elasticity, E, base impedance ZO, as well as ratios and differences of maximum and minimum values of the sampled dz/dt and areas.

An example of alternative means of calculating desired hemodynamic characteristics, as utilized in one embodiment of the illustrated embodiment, determines the desired hemodynamic characteristics based on values determined in the calibrate and sample functions. Thus, the instantaneous rate of blood flow Q can be expressed in terms of the mean area (AMEAN), maximum dz/dt (TADZM), maximum area (AMAX), minimum area (AMIN) and adjustment factor YVF. Cardiac output may then be expressed in terms of instantaneous rate of flow Q integrated over time, or for a one minute sample, $CO = Q \times 60$. The mean of stroke value, VMEAN, may be expressed in terms of the instantaneous rate of flow Q and the mean areas (amean). Body surface area can be calculated based upon height and weight information entered, or a body surface area (BSA) value can be determined externally and input to the system for use. The cardiac index may be expressed in terms of the cardiac output and body surface area. The stroke volume may be expressed in terms of the cardiac output and the heart rate, as determined by the system or as externally input for the system. The pressure differential can be calculated or measured, as described above, and the systemic vascular resistance can be expressed in terms of the pressure differential and the cardiac output (co). The potential energy of blood flow, POWP, can be expressed in terms of the pressure differential and the instantaneous rate of flow Q. The kinetic energy of blood flow, POWEK, may be expressed in terms of mean stroke volume, VMEAN, and the instantaneous rate of flow Q. The total power of the heart may be expressed in terms of the kinetic and potential energy flows of blood, $POWP = POWP + POWEK$. The cardiac power index may be determined in terms of the total power, POW, of the heart and the body surface area. The work may be determined from POW. DZ/DTMIN, TADZN, is determined, and adjusted, according to the input sex data of the patient under tests, to adjust for sex related factors. Ratios may be determined by max to min impedence, max to min dz/dt ratios, differences of max to min impedence and dz/dt values, and other permutations and combinations of previously measured and determined values.

Upon completion of all desired calculations, the report generator function of the system is put into operation. Desired hemodynamic characteristics are displayed, as well as measured and determined values, and, personal data is input by the operator. Display may be my means of a video monitor, a printer, a chart recorder, or other display means. An example of a print out display of desired hemodynamic characteristics, measured parameters, and personal data, is shown in FIG. 28.

Referring to FIG. 28, systolic pressure (Ps), diastolic (Pd), mean arterial pressure ($P_m$), pulse rate (HR), heart cycle time, cardiac output, stroke volume, power, ZO, DZ/DT, sex, age, height, weight, electrode separation, body surface area, date, and patient ID are expressed in absolute terms. Additionally, cardiac index, systemic vascular resistance, cardiac power index, DZ/DT, elastic index, elastic modulus, rate of energy output, rate of impedance change, and rate of pressure change are expressed in terms of absolute value, percent deviation from normal, percent range of normal, and reference parameters listed. Furthermore, additional parameters and values may be displayed, or some of the displayed parameters of FIG. 28 may be deleted, based upon the needs of the operator, and the design of the system.

It is thus seen, that in accordance with the present inventions teachings disclosed herein, a means and method are provided for determining hemodynamic characteristics in a harmless, quick, and simple way. Additionally, the system resulting from utilization of the present invention provides an accurate and highly reproducible hemodynamic parameter determination method and means. Thus, a system utilizing the teachings of the present invention can be utilized in monitoring cardiovascular functions in operating rooms, intensive care units, catheterization labs, as a part of regular check ups, and in any other situation where it is important to determine hemodynamic parameters in an accurate and highly reproducible manner. In the illustrated embodiment, impedance and pressure measurements are done noninvasively, and in conjunction with the teachings of the present invention are utilized to determine the cross sectional area of the blood vessel at any instant of time, the elastic properties of the artery walls, the contractile properties of heart muscle, and numerous hemodynamic characteristics such as cardiac output, cardiac index, stroke volume, systemic vascular resistance, flow through limbs, useful work or power of the left heart, cardiac power index, DZ/DTmin, and other values.

Additionally, in accordance with the teachings of the present invention, and the disclosed illustrated embodiment, continuous monitoring and measurement, and display, of cardiovascular functions can be performed, providing the additional capabilities of monitoring the effects of drug introduction into the blood system over time, and monitoring recovery rates of patients following medication or surgery or injury. By storing data representative of normal and abnormal conditions and by comparing the test results after the use of drugs, such as by pattern recognition techniques, the progress or deterioration of the patient's condition can be noted.

The present system overcomes the problems and inadequacies of prior existing methods, such as lack of accuracy and repeatability, and trauma and injury caused by invasive techniques. Additionally, embodiments utilizing the present invention are capable of determining many more hemodynamic characteristics than have heretofore been determinable from measured values. Furthermore, system embodiments utilizing the present invention, EHD, significantly advance the art beyond impedance plethysmography (which meets with great resistance due to objectives of lack of accuracy and lack of repeatability) yet retain the attractiveness of noninvasive measurement techniques. As discussed earlier herein, any means of determining cross sectional area of the blood vessel may be utilized in place of impedance measurements such as sonic, invasive, etc.

The invention may be particularly useful to do heart stress analysis or analysis of a patient who is ambulatory. The electrodes may be placed on an arm or a leg rather than around the chest, as illustrated. The patient's heart may also be loaded by tilting the table on which the patient is lying to lower the patient's head substantially below his feet and then the results of the tests in this inclined position may be compared to a non-loading or horizontal position of the patient.

Although the invention has been described with reference to specific embodiments, this description is not meant to be construed in a limiting sense. Various modifications of the disclosed embodiment, as well as other embodiments of the invention, will become apparent to persons skilled in the art upon reference to the description of the invention. It is therefore contemplated that the appended claims will cover any such modifications or embodiments as fall within the true scope of the invention.

What is claimed is:

1. A method for measuring a hemodynamic characteristic of a living body having elastic blood vessels comprising the steps of:

measuring a characteristic value across a section of said body, said characteristic value being at least representative of the variation in cross-sectional area of the blood vessels within that section;

measuring blood pressure in said body simultaneously with the measurement of said characteristic value; and processing signals representative of the characteristic value and the blood pressure measurements with a processing means to obtain an electrical signal representing the hemodynamic characteristic; said processing step including the step of utilizing at least one hemodynamic equation which relates said characteristic value, said blood pressure and the modulus of elasticity of the blood vessels within said section as a function, and including the step of calculating said modulus of elasticity.

2. The method as set forth in claim 1 further characterized in that said step of measuring said characteristic value includes measuring the electrical impedance across said section.

3. The method as set forth in claim 2 characterized in that said step of processing includes the step of selecting said hemodynamic formula for the determination of cardiac output over a time period.

4. The method as set forth in claim 2 further comprising the step of selecting said hemodynamic formula for the determination of modulus of elasticity of the arterial walls in said body section.

5. The method as set forth in claim 2 wherein said step of utilizing a hemodynamic equation includes utilizing the equation $$\rho L \left( \frac{1}{Z} - \frac{1}{Zc} \right) = Ao \left( \frac{P}{E'} + 1 \right)^2$$

where
$\rho$ = resistivity of the blood
L = distance of the section over which the impedance is measured
Z = impedance variation due to blood flow variance
Zc = impedance due to the tissue comprising the section
Ao = unstretched cross sectional area of the blood vessels of the section.
P = pressure variation causing the blood flow variance
$E' = (K^2 - 1/K^2 + 1)E$
E = modulus of elasticity for the blood vessels of the section.
K = Ro/Ri the ratio of the outer to the inner diameters of the blood vessels of the section.

6. An apparatus for determining the value of a characteristic of blood flow in a section of a living body having elastic blood vessels comprising:
an inpedance plethysmograph for connection to said body having electrodes for attachment at spaced positions along said section of said body for selectively outputting a signal representative of the value of the electrical impedance of said body section,
means for simultaneously measuring blood pressure of said living body and for outputting a signal representative thereof; and
a processor having means for receiving said signals representing said electrical impedance and said blood pressure, means for storing corresponding values of the blood pressure and electrical impedance signals as a plurality of sets; and means for processing said simultaneously measured sets of said signals with corresponding sets of hemodynamic equations which relate said impedance, said blood pressure, and the modulus of elasticity of the blood vessels within said section as a function so as to calculate said modulus of elasticity, and so as to generate said blood flow characteristic.

7. The apparatus as in claim 6, further comprising:
means for outputting stored values, wherein said processor is additionally responsive to said stored values.

8. The apparatus as set forth in claim 6 including means for displaying the value of said blood flow characteristic.

9. The apparatus as set forth in claim 6 in which said blood flow characteristic is cardiac output.

10. The apparatus as set forth in claim 6 in which said blood flow characteristic is rate of blood flow.

11. The apparatus as set forth in claim 6 in which said blood flow characteristic is a function of the modulus of elasticity of the blood vessels within the body section.

12. The apparatus as set forth in claim 6 in which said blood flow characteristic is contractility of the left ventricle of the heart in said body.

13. The apparatus as in claim 6 further characterized in that said blood flow characteristic is cardiac index.

14. The apparatus as in claim 6 further characterized in that said blood flow characteristic is useful power output of the heart.

15. The apparatus as in claim 6 further characterized in that said blood flow characteristic is systemic vascular resistance.

16. The apparatus as in claim 6 further characterized in that said blood flow characteristic is stroke volume.

17. The apparatus as in claim 6 further characterized in that said blood flow characteristic is cross-sectional area of the blood vessels within the body section.

18. The apparatus as set forth in claim 6 wherein said processor processes simultaneous sets of the equations:

$$\rho L \left( \frac{1}{Z} - \frac{1}{Zc} \right) = Ao \left( \frac{P}{E'} + 1 \right)^2$$

where
$\rho$ = resistivity of the blood
L = distance of the section over which the impedance is measured
Z = impedance variation due to blood flow variance
Zc = impedance due to the tissue comprising the section
Ac = unstretched cross sectional area of the blood vessels of the section.
P = pressure variation causing the blood flow variance
$E' = (K^2 - 1/K^2 + 1)E$
E = modulus of elasticity for the blood vessels of the section.

19. A method of measuring a hemodynamic characteristic across a section of a living body having elastic blood vessels comprising the steps of:
determining the viscosity and resistivity of the blood of the body;
attaching a plethysmograph for measuring an electrical impedance across said section of the body said impedance being at least representative of the variance in the cross sectional area of the blood vessels within said section;
attaching means for measuring blood pressure;
measuring personal characteristics of said body;
processing signals representative of the characteristic value and the blood pressure measurements with a processing means to obtain an electrical signal representing the hemodynamic characteristic; said processing step including the step of utilizing at least one hemodynamic equation which relates said characteristic value, said blood pressure and the modulus of elasticity of the blood vessels within said section as a function, and including the step of calculating said modulus of elasticity; and further processing said personal characteristics with a hemodynamic equation which relates said hemodynamic characteristic as a function of the calculated modulus of elasticity of said blood vessels, said viscosity, said resistivity, and said personal characteristics to determine the hemodynamic characteristic.

20. The method as in claim 19 wherein said personal characteristics are from the class of age, sex, height, and weight.

21. The method as in claim 19 further comprising the step of:

calculating the average cross-sectional area of vessels in the portion of the body as a function of the measured electrical impedance and blood pressure values.

22. The method as in claim 19 wherein said personal characteristic measuring step include the step of taking a blood sample from said body and performing a hematocrit on said sample to determine the viscosity and electrical resistivity of the blood sample.

23. A method of determining the kinetic energy of blood flow through a blood vessel comprising the steps of:

measuring an electrical property across a section of a body overlying the section of the blood vessel, measuring blood pressure in said body simultaneously with the measurement of the electrical property;

processing values representative of multiple sets of the simultaneous measurements of the blood pressure and the electrical property to obtain a first value representing the mean area of the section of the blood vessel, a second value representing the rate of blood flow, and a third value representing the mean blood velocity; and processing values representative of the rate of blood flow and mean blood velocity to obtain a value representing the kinetic energy of blood flow.

24. A method for measuring the total heart power comprising the steps of:

measuring an electrical property across a section of a body overlying the section of the blood vessel, measuring blood pressure in said body simultaneously with the measurement of the electrical property;

processing values representative of multiple sets of the simultaneous measurements of the blood pressure and the electrical property to obtain a first value representing potential energy of blood flow, and a second value representing kinetic energy of blood flow; and processing the values representing the potential and the kinetic energies of the blood flow to determine the value of the total heart power.

25. The method of claim 24 further comprising the steps of:

determining a value representing body surface area, processing the values representing the total heart power and the body surface area to obtain a cardiac power index value representing the total heart power per body surface area.

26. A system for measuring a hemodynamic characteristic comprising:

means for non-invasively measuring a characteristic value across a section of a living body, means for non-invasively measuring blood pressure in said body simultaneously with the measurement of said characteristic value; and means for processing signals representative of the characteristic value and the blood pressure measurements through an electronic device to obtain an electrical signal representing the hemodynamic characteristic.

27. The system as set forth in claim 24 further comprising:

means for displaying the value representative of the hemodynamic characteristic.

28. The system as set forth in claim 27 wherein said measurements are taken over a time period and said display is in the face of a curve.

29. The system as in claim 26 further characterized in that said characteristic value is impedance.

30. The system as set forth in claim 29 wherein said processing is performed by passing signals representing said impedance and blood pressure signals through an electronic device for outputting said electrical signal representing a hemodynamic characteristic in accordance with selected formulae.

31. The system as set forth in claim 30 in which said formulae are selected for the determination of cardiac output over a time period.

32. The system as set forth in claim 30 in which said formulae are selected for the determination of modulus of elasticity of the arterial walls in said body section.

33. An apparatus for measuring hemodynamic characteristics comprising:

means for measuring across a section of a living body and determining a characteristic value;

means for measuring blood pressure in said body simultaneously with the measurement of the characteristic value;

means for determining a hemodynamic characteristics from the simultaneous measurements; and means for displaying the determined hemodynamic characteristics.

34. The apparatus as in claim 33 further comprising:

means for repeating the simultaneous measurements a plurality of times; and means for determining hemodynamic characteristics responsive to the plurality of simultaneous measurements.

35. The apparatus as in claim 33 or 34 further comprising:

means for measuring an electrical characteristic value across the section of living body, and means for determining the characteristic value from the measured electrical characteristic value.

36. The apparatus of claim 35 further characterized in that said electrical characteristic value is a function of electrical impedance Z.

37. The apparatus as in claim 36 further comprising:

means for determining the electrical impedance measurements corresponding to systolic $P_S$ and diastolic $P_D$ blood pressure measurements;

means for determining an elasticity value E from the simultaneous blood pressure and impedance measurements corresponding to systolic and diastolic pressure, and a third pair of simultaneous measurements of pressure and impedance;

means for determining the respective cross sectional area of the vessel for each set of measurements from the respective pressure and impedance measurements and E.

38. The apparatus as in claim 37 further comprising:
means for determining the rate of blood flow Q as a function of the determined elasticity value E and the measured impedances and pressures.

39. The apparatus as in claim 38 further comprising:
means for determining the stroke volume V as a function of the rate of blood flow Q integrated over the time of a cardiac cycle.

40. The apparatus as in claim 38 further comprising:
means for taking a plurality of time-sequential impedance and pressure measurements and averaging said plurality to determine a surface impedance, Z base, a mean pressure, P mean, and a mean elasticity, E mean,
means for deriving a mean area, A mean, responsive to Z base, P mean and E mean; and
means for determining an average velocity of blood responsive to the rate of blood flow Q and the mean area, A mean.

41. The apparatus of claim 35 further characterized in that said electrical characteristic value is the first time derivative dz/dt of the electrical impedance Z.

42. The apparatus as in claim 34 wherein the means for measuring blood pressure is further comprised of:
means for attaching a blood pressure measuring device to the patient's body; and
means for generating signals from the device which vary with time during the cycle of blood flow.

43. The apparatus as in claim 34 or 42 wherein said means for measuring said characteristic value is further comprised of:
means for attaching first and second electrode sets in spaced relationship to one another across the section of the body;
means for injecting an electrical signal into said first electrode set;
means for detecting an electrical signal as received by said second electrode set; and
means for outputting said signal representative of said characteristic value.

44. A system for measuring and determining a hemodynamic characteristic comprising:
means for determining viscosity and resistivity of blood of a patient;
means for attaching a plethysmograph to measure an electrical property across a portion of the patient's body, means for simultaneously measuring blood pressure and the electrical property across the section of the patient;
means for inputting personal characteristics of the patient; and
means for processing the personal characteristics and the simultaneously measured values of the blood pressure and the electrical property, to determining the hemodynamic characteristic.

45. The system as in claim 44 wherein said personal characteristics are from the class of the patient's age, sex, height, and weight.

46. The system as in claim 44 further comprising:
means for calculating the average cross-sectional area of vessels in the portion of the body as a function of the measured electrical property and blood pressure values.

47. The system as in claim 44 wherein said electrical property is impedance.

48. The system as in claim 44 further comprising means for taking a blood sample and determining a hemotocrit therefrom.

49. A system for measuring the cross-sectional area of a section of a blood vessel comprising:
means for measuring an electrical property across a section of a body overlying the section of the blood vessel,
means for measuring blood pressure in said body simultaneously with the measurement of the electrical property,
means for processing values representative of the simultaneous measurements of the blood pressure and the electrical property to obtain a value representing the cross-sectional area of the section of the blood vessel.

50. A system for measuring the elasticity of a section of a blood vessel comprising:
means for measuring an electrical property across a section of a body overlying the section of the blood vessel,
means for measuring blood pressure in said body simultaneously with the measurement of the electrical property, and
means for processing values representative of multiple sets of the simultaneous measurements of the blood pressure and the electrical property to obtain a value representing the elasticity of the section of the blood vessel.

51. A system for measuring the rate of blood flow in a section of a blood vessel comprising:
means for measuring an electrical property across a section of a body overlying the section of the blood vessel,
means for measuring blood pressure in said body simultaneously with with the measurement of the electrical property, and
means for processing values representative of multiple sets of simultaneous measurements of the blood pressure and the electrical property to obtain a value representing the rate of blood flow in the section of the blood vessel.

52. The system as in claim 51 further comprising:
means for integrating the rate of blood flow over the time of one cardiac cycle to determine pulse stroke volume.

53. The system as in claim 51 further comprising:
means for integrating the rate of blood flow over one minute to determine cardiac output.

54. The system as in claim 53 further comprising:
means for determining a value for the body surface area, and
means for determining a cardiac index as a function of the cardiac output and the body surface area.

55. The system as in claim 53 further comprising:
means to determining heart rate;
means for determining stroke volume as a function of the cardiac output divided by the heart rate.

56. A system for measuring the mean velocity of blood across a section of a blood vessel comprising:
means for noninvasively measuring an electrical property across a section of a body overlying the section of the blood vessel,
means for noninvasively measuring blood pressure in said body simultaneously with the measurement of the electrical property;
means for processing values representative of multiple sets of the simultaneous measurements of the blood pressure and the electrical property to obtain a value representing the mean area of the section of the blood vessel;

means for processing values representative of multiple sets of the simultaneous measurements to obtain a value representating the rate of blood flow in the section of the blood vessel, and means for deriving the mean velocity of blood responsive to the rate of blood and the mean area.

57. The system as in claim 56 further comprising means for displaying the mean velocity of blood, rate of blood flow, and mean area.

58. A system for measuring vascular resistance comprising:

means for measuring blood pressure in said body at two points on said body, overlying said section;

means for processing values representative of the two-point measurements of the blood pressure to obtain a value representing differential blood pressure of the section of the blood vessel, means for determining cardiac output; and means for determining vascular resistance as a function of the cardiac output and the differential blood pressure.

59. The method as in claim 58 wherein the vascular resistance is systemic; and the two points measured are mean right artial pressure and mean arterial pressure.

60. The system as in claim 58 further comprising:

means for detemining the rate of blood flow, and means for determining a value for the potential energy of blood flow as a function of the differential blood pressure and the rate of blood flow.

61. A system for determining the kinetic energy of blood flow through a blood vessel comprising:

means for measuring an electrical property across a section of a body overlying the section of the blood vessel, means for measuring blood pressure in said body simultaneously with the measurement of the electrical property;

means for processing values representative of multiple sets of the simultaneous measurements of the blood pressure and the electrical property to obtain a first value representing the rate of blood flow, and a second value representing the mean blood velocity; and means for processing values representative of the rate of blood flow and mean blood velocity to obtain a value representing the kinetic energy of blood flow.

62. A system for measuring the total heart power comprising:

means for measuring an electrical property across a section of a body overlying the section of the blood vessel, means for measuring blood pressure in said body simultaneously with the measurement of the electrical property;

means for processing values representative of multiple sets of the simultaneous measurements of the blood pressure and the electrical property to obtain a first value representing potential energy of blood flow, and a second value representing kinetic energy of blood flow; and means for processing the values representing the potential and the kinetic energies of blood flow to determine the value of the total heart power.

63. The system of claim 62 further comprising:

means for determining a value representing body surface area, and means for processing the values representing the total heart power and the body surface area to obtain a value representing the total heart power per body surface area.

64. A method for measuring a hemodynamic characteristic in a section of a living body having elastic blood vessels comprising:

measuring an electrical parameter across said body section to determine an impedance value for said section;

measuring a blood pressure value in said body simultaneously with the measurement of the impedance value;

determining impedance values corresponding to the systolic and the diastolic blood pressure of the body;

calculating an elasticity value E from the simultaneous blood pressure and impedance measurements corresponding to said systolic and diastolic pressures, and a third pair of measurements of mean pressure and impedance, and determining the respective cross sectional area of the blood vessels within said section for each set of measurements from the respective pressure and impedance measurements and E.

65. The method as set forth in claim 64 further comprising the step of:

determining the rate of blood flow Q as a function of the determined elasticity value E and the measured impedances and pressures.

66. The method as in claim 65 further comprising the step of:

determining the stroke volume V as a function of the rate of blood flow Q integrated over a fixed time t of a cardiac cycle.

67. The method as in claim 65 further comprising the step of:

determining cardiac output as a function of the rate of blood flow Q integrated over a set of predetermined limits.

68. The method as in claim 65 wherein the step of measuring blood pressure further comprises:

attaching a blood pressure measuring device to said body; and generating signals from the device which vary with time during the cycle of blood flow.

69. The method as set forth in claim 68 wherein the step of measuring said characteristic value is further comprised of the steps of:

attaching a first electrode set and second electrode set to said body in spaced relationship to one another;

injecting an electrical signal into said first electrode set;

detecting an electrical signal as received by said second electrode set; and outputting said signal representative of said representative value.

70. The method as set forth in claim 64 further comprising the steps of:

taking a plurality of time-sequential impedance and pressure measurements and averaging said plurality to determine a base impedance, Z base, a mean pressure, P mean, and a mean elasticity, E mean, deriving a mean area, A mean, corresponding to Z base, P mean and E mean; and, determining an average velocity of blood corresponding to Z base, P mean and E mean; and,
determining an average velocity of blood corresponding to Q and A mean.

71. A method for measuring the instantaneous rate of blood flow in a section of a living body having elastic blood vessels comprising the steps of:
 measuring an electrical parameter across a section of said body having the blood vessels within, said electrical property being at least representative of the variance in cross sectional area of the blood vessels within that section;
 measuring blood pressure in said body simultaneously with the measurement of said electrical parameter;
 processing values of multiple sets of simultaneous measurements of the blood pressure and the electrical parameter;
 solving a set of hemodynamic equations which relates the axial velocity of the blood in said vessels as a function of various unknowns, said equations having of the same number of unknown variables as the number of measurement sets, wherein one of the unknowns is the modulus of elasticity of the blood vessels within said section;
 multiplying the axial velocity of the blood flow by the cross sectional area of the blood vessels of said section to yield an instantaneous rate of blood flow therethrough.

72. The method as set forth in claim 71 further comprising the step of:
 integrating the rate of blood flow over a predetermined period to determine cardiac output.

73. The method as in claim 72 further comprising the step of:
 determining the heart rate; and
 determining stroke volume as a function of the cardiac output divided by the heart rate.

74. A method as set forth in claim 73 comprising:
 measuring blood pressure in said body at two points, on said body;
 processing values representative of the two-point measurement of the blood pressure to obtain a value representing differential blood pressure of the blood vessels of said section,
 determining cardiac output; and
 determining vascular resistance as a function of the cardiac output and the differential blood pressure.

75. The method as in claim 73 wherein the vascular resistance is sytemic; and the two points measured are mean right atrial pressure and mean arterial pressure.

76. The method as in claim 74 further comprising the steps of:
 determining the instantaneous rate of blood flow, and
 determining a value for the potential energy of blood flow due to the power output of the heart as a function of the differential blood pressure and the rate of blood flow.

77. The method as in claim 74 further comprising the step of:
 measuring blood pressure in said body at said mean right atrial pressure and pressure at a point at any other artery.

78. The method as set forth in claim 74 further comprising the step of integrating the rate of blood flow over one cardiac cycle to determine stroke volume.

79. The method as in claim 71 further comprising the steps of:
 determining a value for the body surface area, and
 determining a cardiac index as a function of the cardiac output and the body surface area.

80. The system as in claim 26 or 33 or 34 or 44 or 40 or 50 or 51 or 56 or 58 or 61 or 62 further comprising:
 means for displaying the hemodynamic characteristic in a format from the class of formats of absolute values, relative values, deviation from mean, range of values, time averaged values, minimum values, average minimum values, mean values, maximum values, average maximum values, instantaneous rate of change of values, maximum rate of change of values, minimum rate of change of values, mean rate of change of values, and average rate of change of values.

* * * * *